United States Patent
Gupta et al.

(10) Patent No.: US 12,053,729 B2
(45) Date of Patent: *Aug. 6, 2024

(54) REDUCTION OF LEACHABLE BETA-GLUCAN LEVELS FROM CELLULOSE-CONTAINING FILTER MATERIALS

(71) Applicant: EMD Millipore Corporation, Burlington, MA (US)

(72) Inventors: Akshat Gupta, Tewksbury, MA (US); Dana Kinzlmaier, Concord, MA (US); Kara Pizzelli, Hingham, MA (US); Elizabeth Goodrich, Bedford, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/334,925

(22) Filed: Jun. 14, 2023

(65) Prior Publication Data

US 2023/0321574 A1 Oct. 12, 2023

Related U.S. Application Data

(63) Continuation of application No. 17/235,071, filed on Apr. 20, 2021, now Pat. No. 11,712,647, which is a (Continued)

(51) Int. Cl.
*B01D 37/02* (2006.01)
*B01D 39/18* (2006.01)
(Continued)

(52) U.S. Cl.
CPC .......... *B01D 39/18* (2013.01); *B01D 37/025* (2013.01); *B01D 71/10* (2013.01); *C12M 37/02* (2013.01); *D21C 9/004* (2013.01); *D21C 9/005* (2013.01)

(58) Field of Classification Search
CPC ...... B01D 37/02; B01D 37/025; B01D 39/16; B01D 39/1607; B01D 39/1615; (Continued)

(56) References Cited

U.S. PATENT DOCUMENTS 1,734,516 A  11/1929  Percy et al.
2,207,076 A  7/1940  Spurlin
(Continued)

FOREIGN PATENT DOCUMENTS

CN  102741477 A  10/2012
EP  0094165 A2  11/1983
(Continued)

OTHER PUBLICATIONS

Sayar et al., "In vitro binding of flours from oat lines varying in percentage and molecular weight distribution of β-glucan", Journal of Agricultural and Food Chemistry, vol. 53, 2005, pp. 8798-8803.
(Continued)

*Primary Examiner* — Joseph W Drodge
(74) *Attorney, Agent, or Firm* — EMD Millipore Corporation

(57) ABSTRACT

Treatment methods for reduction of (1→3)-β-D-glucan leachables from cellulose-containing filter materials are described.

18 Claims, 13 Drawing Sheets

Related U.S. Application Data continuation of application No. 16/316,890, filed as application No. PCT/US2017/057878 on Oct. 23, 2017, now Pat. No. 11,014,031.

(60) Provisional application No. 62/413,013, filed on Oct. 26, 2016.

(51) Int. Cl.
*B01D 71/10* (2006.01)
*C12M 1/12* (2006.01)
*D21C 9/00* (2006.01)

(58) Field of Classification Search
CPC .... B01D 39/1623; B01D 39/18; B01D 71/10; B01D 71/12; B01D 71/16; B01D 71/18; B01D 2239/0492; B01D 2239/12; B01D 2257/70; B01D 2311/12; B01D 2311/2688; B01D 2315/06; B01D 2321/16; B01D 2321/162; B01D 2321/168; B01D 2239/10; B01D 2273/18; A61K 35/16; D21C 9/004; D21C 9/005; C12M 33/14; C12M 37/02; C12M 47/12
USPC .............. 210/767, 777, 193, 500.29–500.32, 210/503–508
See application file for complete search history.

(56) References Cited

U.S. PATENT DOCUMENTS

| | | | |
|---|---|---|---|
| 2,495,233 | A | 1/1950 | Nicolas et al. |
| 3,580,841 | A | 5/1971 | Cadotte et al. |
| 3,816,150 | A | 6/1974 | Ishii et al. |
| 4,606,824 | A | 8/1986 | Chu |
| 4,830,885 | A * | 5/1989 | Tran .......................... G05B 5/01 210/500.33 |
| 5,085,784 | A | 2/1992 | Ostreicher |
| 5,098,569 | A | 3/1992 | Stedronsky |
| 5,114,537 | A | 5/1992 | Scott et al. |
| 5,150,723 | A | 9/1992 | Lee et al. |
| 7,337,782 | B2 | 3/2008 | Thompson |
| 11,014,031 | B2 | 5/2021 | Gupta et al. |
| 11,712,647 | B2 * | 8/2023 | Gupta ..................... B01D 71/10 210/500.29 |
| 2005/0247419 | A1 | 11/2005 | Hamed et al. |
| 2006/0286296 | A1 | 12/2006 | Brandt et al. |
| 2011/0003982 | A1 | 1/2011 | Mazoyer et al. |
| 2012/0298319 | A1 | 11/2012 | Fujiwara et al. |
| 2015/0068978 | A1 | 3/2015 | Lando et al. |
| 2016/0177512 | A1 | 6/2016 | Kawahara et al. |
| 2019/0224600 | A1 | 7/2019 | Gupta et al. |

FOREIGN PATENT DOCUMENTS

| | | |
|---|---|---|
| EP | 1663444 B1 | 10/2007 |
| EP | 2226171 A1 | 9/2010 |
| EP | 2532782 A1 | 12/2012 |
| JP | S58-207918 A | 12/1983 |
| JP | S61-44824 A | 3/1986 |
| JP | H11-243939 A | 9/1999 |
| JP | 2007-014854 A | 1/2007 |
| JP | 2007-307513 A | 11/2007 |
| JP | 2008-274525 A | 11/2008 |
| JP | 2013-106520 A | 6/2013 |
| WO | 2018/080999 A1 | 5/2018 |

OTHER PUBLICATIONS

Schneeman, "Dietary fibre and gastrointestinal function", In Book: Advanced Dietary Fibre Technology, 2001, pp. 168-173.

Seger et al., "Structure of cellulose in cuoxam", Macromolecular Symposia, vol. 83, No. 1, 1994, pp. 291-310.

Sekkal et al., "Investigation Of The Glycosidic Linkages In Several Oligosaccharides Using Ft-ir And Ft Raman Spectroscopies", Journal of Molecular Structure, vol. 349, Apr. 1, 1995, pp. 349-352.

Selvendran et al., "Determination Of Aldoses And Uronic Acid Content Of Vegetable Fiber", Analytical Biochemistry, vol. 96, No. 2, Jul. 15, 1979, pp. 282-292.

Skendi et al., "Structure And Rheological Properties Of Water Soluble B-glucans From Oat Cultivars Of Avena Sativa And Avena Bysantina", Journal of Cereal Science, vol. 38, No. 1,, 2003, pp. 15-31.

Soga et al., "Determination Of Carbohydrates In Food Samples By Capillary Electrophoresis With Indirect UV Detection", Food Chemistry, vol. 69, No. 3, May 15, 2000, pp. 339-344.

Staudte et al., "Water-soluble (1→3), (1→4)-β-d-glucans from barley (*Hordeum vulgare*) endosperm. III. Distribution of cellotriosyl and cellotetraosyl residues", Carbohydrate Polymers, vol. 3, No. 4, 1983, pp. 299-312.

Storsley et al., "Structure And Physicochemical Properties Of B-glucans And Arabinoxylans Isolated From Hull-less Barley", Food Hydrocolloids, vol. 17, No. 6, 2003, pp. 831-844.

Sundberg et al., "Mixed-Linked B-Glucan From Breads Of Different Cereals Is Partly Degraded In The Human Ileostomy Model", The American Journal of Clinical Nutrition, vol. 64, No. 6, Dec. 1, 1996, pp. 878-885.

Suortti, "Size-exclusion Chromatographic Determination Of B-glucan With Postcolumn Reaction Detection", Journal of Chromatography A, vol. 632, Feb. 19, 1993, pp. 105-110.

Talaga et al., "Development of a high-performance anion-exchange chromatography with pulsed-amperometric detection based quantification assay for pneumococcal polysaccharides and conjugates", Vaccine, vol. 20, Jun. 7, 2002, pp. 2474-2484.

Tappy et al., "Effects Of Breakfast Cereals Containing Various Amounts Of B-glucan Fibers On Plasma Glucose And Insulin Responses In Niddm Subjects", Diabetes Care, vol. 19, 1996, pp. 831-834.

Theander et al., "Studies on dietary fibres", Swedish Journal of Agricultural Research, vol. 9, 1979, pp. 97-106.

Tosh et al., "Evaluation Of Structure In The Formation Of Gels By Structurally Diverse (1→3)(1→4)-β-d-glucans From Four Cereal And One Lichen Species", Carbohydrate Polymers, vol. 57, Sep. 13, 2004, pp. 249-259.

Tosh et al., "Structural Characteristics And Rheological Properties Of Partially Hydrolyzed Oat B-glucan: The Effects Of Molecular Weight And Hydrolysis Method", Carbohydrate Polymers, vol. 55, No. 4, Mar. 15, 2004, pp. 425-436.

Tvaroska et al., "Crystalline conformation and structure of lichenan and barley β-glucan", Canadian Journal of Chemistry, vol. 61, 1983, pp. 1608-1616.

Vaikousi et al., "Solution Flow Behavior And Gelling Properties Of Water-soluble Barley (1→3,1→4)-β-glucans Varying In Molecular Size", Journal of Cereal Science, vol. 39, No. 1, 2004, pp. 119-137.

Varum et al., "Light Scattering Reveals Micelle-like Aggregation In The (1→3),(1→4)-β-d-glucans From Oat Aleurone", Food Hydrocolloids, vol. 5, 1992, pp. 497-511.

Vasanthan et al., "Dietary Fiber Profile Of Barley Flour As Affected By Extrusion Cooking", Food Chemistry, vol. 77, No. 1, 2002, pp. 35-40.

Vigor et al., "Development of downstream processing to minimize beta-glucan impurities of GMP-manufactured antibodies", Biotechnology Progress, vol. 32, No. 6, Oct. 21, 2016, pp. 1494-1502.

Virkki et al., "Structural characterization of water-insoluble nonstarchy polysaccharides of oats and barley", Carbohydrate Polymers, vol. 59, Jan. 29, 2004, pp. 357-366.

Wang et al., "Impact of residual impurities and contaminants on protein stability", Journal of pharmaceutical sciences, vol. 103, No. 5, Feb. 18, 2014, pp. 1315-1330.

Wang et al., "The Changes Of B-Glucan Content And B-glucanase Activity In Barley Before And After Malting And Their Relationships To Malt Qualities", Food Chemistry, vol. 86, No. 2, 2004, pp. 223-228.

Welch et al., "Chemical composition of oats", In Book: The oat crop. Production and utilization, 1995, pp. 279-320.

(56) References Cited

OTHER PUBLICATIONS

Westerlund et al., "Isolation And Chemical Characterization Of Water-soluble Mixed-linked B-glucans And Arabinoxylans In Oat Milling Fractions", Carbohydrate Polymers, vol. 20, No. 2, 1993, 1993, pp. 115-123.

Wilhelmson et al., "Development Of A Germination Process For Producing High B-glucan Whole Grain Food Ingredients From Oat", Cereal Chemistry, vol. 78, No. 6, 2001, pp. 715-720.

Williams et al., "Introduction to food hydrocolloids", In Book: Handbook of Hydrocolloids, 2002, pp. 1-19.

Wohlsen et al., "Evaluation of Five Membrane Filtration Methods for Recovery of Cryptosporidium and Giardia Isolates from Water Samples", Applied and Enviromental Microbiology, vol. 70, No. 4, 2004, pp. 2318-2322.

Wood, P. J., "Cereal B-glucans: Structure, Properties And Health Claims.", In Book: Advanced Dietary Fibre Technology, 2001, pp. 315-327.

Wood et al., "Comparisons of viscous properties of oat and guar gum and the effects of these and oat bran on glycemic index", Journal of Agricultural and Food Chemistry, vol. 38, 1990, pp. 753-757.

Wood et al., "Effect Of Dose And Modification Of Viscous Properties Of Oat Gum On Plasma Glucose And Insulin Following An Oral Glucose Load", British Journal of Nutrition, vol. 72, 1994, pp. 731-743.

Wood, P. J., "Evaluation Of Oat Bran As A Soluble Fibre Source. Characterization Of Oat B-glucan And Its Effects On Glycaemic Response", Carbohydrate Polymers, vol. 25, No. 4, 1994, pp. 331-336.

Wood et al., "Evaluation Of Role Of Concentration And Molecular Weight Of Oat B-glucan In Determining Effect Of Viscosity On Plasma Glucose And Insulin Following An Oral Glucose Load", British Journal of Nutrition, vol. 84, 2000, pp. 192-23.

Wood et al., "Large-Scale Preparation and Properties of Oat Fractions Enriched in (1-3)(1-4)-Beta-D-Glucan", Cereal Chemistry, vol. 66, No. 2, 1989, pp. 97-103.

Wood et al., "Molecular Characterization of Cereal Beta-Giucans. II. Size-Exclusion Chromatography for Comparison of Molecular Weight", Cereal Chemistry, vol. 68, 1991, pp. 530-536.

Wood et al., "Molecular characterization of cereal β-D-glucans. Structural analysis of oat β-D-glucan and rapid structural evaluation of β-D-glucans from different sources by high-performance liquid chromatography of oligosaccharides released by lichenase", Cereal Chemistry, vol. 68, 1991, pp. 31-39.

Wood et al., "Physicochemical characteristics and physiological properties of oat (1→ 3),(1→ 4)-β-D-glucan", Oat Branley, 1993, pp. 83-112.

Wood, P. J., "Relationships Between Solution Properties Of Cereal B-glucans And Physiological Effects", Trends in Food Science & Technology, vol. 15, 2004, pp. 313-320.

Wood et al., "Structural Studies of (1-3)(1-4)-beta-D-Glucans by 13C-Nuclear Magnetic Resonance Spectroscopy and by Rapid Analysis of Cellulose-Like Regions Using High-Performance Anion-Exchange Chromatography of Oligosaccharides Released by Lichenase", Cereal Chemistry, vol. 71, 1994, pp. 301-307.

Wood et al., "Studies on the specificity of interaction of cereal cell wall components with Congo Red and Calcofluor. Specific detection and histochemistry of (1→3),(1→4)-β-D-glucan", Journal of Cereal Science, vol. 1, No. 2, 1983, pp. 95-110.

Wood et al., "Use of Calcofluor in analysis of oat beta-D-glucan", Cereal Chemistry, vol. 61, 1984, pp. 73-75.

Woodward et al., "Water-soluble (1→3), (1→4)-β-d-glucans From Barley (*Hordeum vulgare*) Endosperm. I. Physicochemical Properties", Carbohydrate Polymers, vol. 3, No. 2,, 1983, pp. 143-156.

Woodward et al., "Water-soluble (1→3), (1→4)-β-d-glucans From Barley (*Hordeum vulgare*) Endosperm. Ii. Fine Structure", Carbohydrate Polymers, vol. 3, No. 3,, 1983, pp. 207-225.

Yayin, L., "Optimization of Sodium Carbonate-Sodium Hydroxide Pulping of Wheat Straw for Corrugating Medium Production", Western Michigan University, Master's Theses, 954, Apr. 1992, 250 pages.

Yulp et al., "Carbohydrate composition analysis of bacterial polysaccharides: Optimized acid hydrolysis conditions for HPAEC-PAD analysis", Analytical Biochemistry, vol. 201, No. 2, 1992, pp. 343-349.

Yun et al., "β-Glucan, Extracted From Oat, Enhances Disease Resistance Against Bacterial And Parasitic Infections", FEMS Immunology & Medical Microbiology, vol. 35, Jan. 1, 2003, pp. 67-75.

Zhang et al., "Glycerol carbonate as green solvent for pretreatment of sugarcane bagasse", Biotechnology for Biofuels, vol. 6 (153), 2013, 10 pages.

Zhang et al., "Rheological Properties of (1→3),(1→4)-β-d-Glucans from Raw, Roasted, and Steamed Oat Groats", Cereal Chemistry, vol. 75, 1998, pp. 433-438.

Zygmunt et al., "Enzymatic Method For Determination Of (1→3),(1→4)-β-D-Glucans In Grains And Cereals", Journal of AOAC International, vol. 76, 1993, pp. 1069-1082.

U.S. Appl. No. 17/235,071, filed Apr. 20, 2021, Allowed.

Office Action received for Korean Patent Application No. 10-2022-7042595 mailing date Sep. 4, 2023, 6 Pages (2 Pages of English Translation & 4 Pages of Official Copy).

Kacurakova et al., "Developments In Mid-infrared Ft-ir Spectroscopy Of Selected Carbohydrates", Carbohydrate Polymers, vol. 44, No. 4, 2001, pp. 291-303.

Kacurakova et al., "FT-IR Study Of Plant Cell Wall Model Compounds: Pectic Polysaccharides And Hemicelluloses", Carbohydrate Polymers, vol. 43, No. 2, 2000, pp. 195-203.

Kačuráková et al., "Infrared Study Of Arabinoxylans", Journal of the Science of Food and Agriculture, vol. 66, No. 3, 1994, pp. 423-427.

Kahlon et al., "Cholesterol-lowering Effects In Hamsters Of B-glucan-enriched Barley Fraction, Dehulled Whole Barley, Rice Bran, And Oat Bran And Their Combinations", 1993, pp. 435-440.

Kahlon, T., "Cholesterol-Lowering Properties of Cereal Fibres and Fractions", Chapter:18 In Book Advanced Dietary Fibre Technology, 2001, pp. 206-220.

Kalra et al., "Effect of Dietary Barley β-Glucan on Cholesterol and Lipoprotein Fractions in Rat", Journal of Cereal Science, vol. 31, No. 2, 2000, pp. 141-145.

Karppinen et al., "In Vitro Fermentation Of Polysaccharides Of Rye, Wheat And Oat Brans And Inulin By Human Faecal Bacteria", Journal of the Science of Food and Agriculture, vol. 80, No. 10, 2000, pp. 1469-1476.

Kerckhoffs et al., "Cholesterol-lowering effect of β-glucan from oat bran in mildly hypercholesterolemic subjects may decrease when β-glucan is incorporated into bred and cookies", The American Journal of Clinical Nutrition, 2003, pp. 221-227.

Krevelen et al., "Typology of Polymers", In Book: Properties of Polymers, 1990, pp. 7-41.

Laine et al., "Methylation Analysis as a Tool for Structural Analysis of Wood Polysaccharides", Holzforschung, vol. 56, No. 6, 2002, pp. 607-614.

Lambo et al., "Dietary fibre in fermented oat and barley rich concentrates", Food Chemistry, vol. 89, No. 2, 2005, pp. 283-293.

Larsson et al., "On-line Capillary Electrophoresis With Mass Spectrometry Detection For The Analysis Of Carbohydrates After Derivatization With 8-aminonaphthalene-1,3,6-trisulfonic Acid", Journal of Chromatography A, vol. 934, Nov. 16, 2001, pp. 75-85.

Lazaridou et al., "A Comparative Study On Structure-function Relations Of Mixed-linkage (1→3), (1→4) Linear B-d-glucans", Food Hydrocolloids, vol. 18, No. 5, 2004, pp. 837-855.

Lazaridou et al., "Molecular Size Effects On Rheological Properties Of Oat B-glucans In Solution And Gels", Food Hydrocolloids, vol. 17 No. 5, 2003, pp. 693-712.

Lebet et al., "Neutral-Sugar Determination By HPAEC-PAD To Characterize Polysaccharide Degradation By Colonic Bacteria", European Food Research and Technology, vol. 205, 1997, pp. 257-261.

(56) References Cited

OTHER PUBLICATIONS

Lee et al., "Physicochemical Properties of Depolymerized Barley β-Glucan by Alkali Hydrolysis", The Korean Journal of Food And Nutrition vol. 26, No. 3, 2013, pp. 601-607.
Lefebvre et al., "Rheological Behavior of Polysaccharides Aqueous Systems", In Book: Polysaccharides. Structural Diversity and Functional Versatility, 2005, pp. 357-394.
Lia et al., "Oat Beta-glucan Increases Bile Acid Excretion And A Fiber-rich Barely Fraction Increases Cholesterol Excretion In Ileostomy Subjects", The American Journal of Clinical Nutrition, vol. 62, 1995, pp. 1245-1251.
Liu et al., "Recovery and Purification Process Development For Monoclonal Antibody Production", mAbs, Landes Bioscience, vol. 2, No. 5, Oct. 2010, pp. 480-499.
Macgregor et al., "Carbohydrates of the barley grain", Barley: chemistry and technology., 1993, pp. 73-130.
Malkki et al., "Gastrointestinal Effects of Oat Bran and Oat Gum: A Review", LWT—Food Science and Technology, vol. 34, No. 6, 2001, pp. 337-347.
Manthey et al., "Soluble and Insoluble Dietary Fiber Content and Composition in Oat", Cereal Chemistry, vol. 76, No. 3, 1999, pp. 417-420.
Margareta et al., "Importance of processing for physico-chemical and physiological properties of dietary fibre", Proceedings of the Nutrition Society, vol. 62, 2003, pp. 187-192.
Mårtensson et al., "The effect of yoghurt culture on the survival of probiotic bacteria in oat-based, non-dairy products", Food Research International, vol. 35, Issue 8, 2002, pp. 775-784.
Mccleary et al., "Measurement of $(1\rightarrow3),(1\rightarrow4)$-β-D-glucan in barley and oats: A streamlined enzymic procedure", Journal of the Science of Food and Agriculture, vol. 55, No. 2, 1991, pp. 303-312.
Miller et al., "Distribution of $(1\rightarrow3),(1\rightarrow4)$-β-D-glucan in kernels of oats and barley using microspectrofluorometry", Cereal Chemistry, vol. 71, No. 1, 1994, pp. 64-68.
Miller et al., "Mixed linkage β-glucan, protein content, and kernel weight in *Avena* species", Cereal Chemistry, vol. 70, No. 2, 1993, pp. 231-233.
Miller et al., "Oat endosperm cell walls: II. Hot-water solubilisation and enzymatic digestion of the wall", Cereal Chemistry, vol. 72, 1995, pp. 428-432.
Miron et al., "Composition and in vitro digestibility of monosaccharide constituents of selected byproduct feeds", Journal of Agricultural and Food Chemistry, vol. 49, 2001, pp. 2322-2326.
Morgan et al., "A 13C CP/MAS NMR spectroscopy and AFM study of the structure of Glucagel™, a gelling β-glucan from barley", Carbohydrate Research, vol. 315, Jan. 31, 1999, pp. 169-179.
Morgan, K., "Cereal β-glucans", In Book: Handbook of Hydrocolloids, 2000, pp. 287-307.
Olson et al., "Monosaccharides produced by acid hydrolysis of selected foods, dietary fibers, and fecal residues from white and whole wheat bread consumed by humans", Journal of Agricultural and Food Chemistry, vol. 36, No. 2, 1988, pp. 300-304.
Oscarsson et al., "Chemical Composition of Barley Samples Focusing on Dietary Fibre Components", Journal of Cereal Science, vol. 24, 1996, pp. 161-170.
Panagiotopoulos et al., "Sub-ambient temperature effects on the separation of monosaccharides by high-performance anion-exchange chromatography with pulse amperometric detection: Application to marine chemistry", Journal of Chromatography A, vol. 920, Jun. 22, 2001, pp. 13-22.
Papageorgiou et al., "Water extractable $(1\rightarrow3,1\rightarrow4)$-β-d-glucans from barley and oats: An intervarietal study on their structural features and rheological behaviour", Journal of Cereal Science, vol. 42, 2005, pp. 213-224.
International Search Report and Written Opinion received for PCT Application No. PCT/US2017/057878, mailing date Feb. 28, 2018,, Feb. 28, 2018, 15 page.
Pettersen, Rogerc. , "Wood sugar analysis by anion chromatography", Journal of Wood Chemistry and Technology, vol. 11, 1991, pp. 495-501.

Pizzoferrato et al., "Solid-state 13C CP MAS NMR spectroscopy of mushrooms gives directly the ratio between proteins and polysaccharides", Journal of Agricultural and Food Chemistry, vol. 48, 2000, pp. 5484-5488.
Poutanen, Kaisa, "Effect of processing on the properties of dietary fibre", In Book: Advanced Dietary Fibre Technology, 2001, pp. 277-282.
Proniewicz et al., "FT-IR and FT-Raman study of hydrothermally degradated cellulose", Journal of Molecular Structure, vol. 596, Sep. 26, 2001, pp. 163-169.
Puls, J., "Substrate analysis of forest and agricultural wastes", In Book: Bioconversion of Forest and Agricultural Wastes, 1993, pp. 13-32.
El- Rassi, Z. , "Chapter: 2 Reversed-phase and hydrophobic interaction chromatography of carbohydrates and glycoconjugates", Journal of Chromatography Library, vol. 66, 2002, 2002, pp. 41-102.
Rimsten et al., "Determination of β-Glucan Molecular Weight Using SEC with Calcofluor Detection in Cereal Extracts", Cereal Chemistry, vol. 80, Jul. 15, 2003, pp. 485-490.
Ripsin et al., "Oat products and lipid lowering. A Meta-Analysis", JAMA The Journal of the American Medical Association, vol. 267, Jun. 24, 1992, pp. 3317-3325.
Robertson et al., "Solubilisation of Mixed Linkage $(1\rightarrow3), (1\rightarrow4)$β-D-glucans From Barley: Effects of Cooking and Digestion", Journal of Cereal Science, vol. 25, No. 3, 1997, pp. 257-283.
Roubroeks et al., "Molecular Weight, Structure And Shape Of Oat $(1\rightarrow3),(1\rightarrow4)$-β-d-glucan Fractions Obtained By Enzymatic Degradation With $(1\rightarrow4)$-β-d-glucan 4-glucanohydrolase From Trichodermareesei", Carbohydrate Polymers, vol. 46, No. 3, Nov. 3, 2001, pp. 275-285.
Roubroeks et al., "Structural features of $(1\rightarrow3),(1\rightarrow4)$-β-d-glucan and arabinoxylan fractions isolated from rye bran", Carbohydrate Polymers, vol. 42, No. 1, 2000, pp. 3-11.
Saastamoinen et al., "Genetic And Environmental Variation In B-glucan Content Of Oats Cultivated Or Tested In Finland", Journal of Cereal Science, vol. 16, No. 3, 1992, pp. 279-290.
Saastamoinen et al., "ß-Glucan Contents Of Groats Of Different Oat Cultivars In Official Variety, In Organic Cultivation, And In Nitrogen Fertilization Trials In Finland", Agricultural and Food Science, vol. 13, 2004, pp. 68-79.
Salvador et al., "Monosaccharide Composition of Sweetpotato Fiber and Cell Wall Polysaccharides from Sweetpotato, Cassava, and Potato Analyzed by the High-Performance Anion Exchange Chromatography with Pulsed Amperometric Detection Method", Journal of Agricultural and Food Chemistry, vol. 48, 2000, pp. 3448-3454.
Extended European Search Report for EP Patent Application No. 20212177.8 mailing date Jun. 9, 2021, 10 pages.
Notice of Final Rejection issued in Korean Patent Application No. 10-2021-7033983 mailing date Mar. 10, 2022, 7 pages. (4 pages of Official Copy & 3 pages of English Translation).
Office Action received for Korean Patent Application No. 10-2021-7033983, mailing date Jul. 18, 2022, 10 Pages (5 Pages of English translation & 5 Pages of Official copy).
Non Final Office Action Received for U.S. Appl. No. 17/235,071, mailing date Nov. 25, 2022, 12 Pages.
Notice of Allowance received for U.S. Appl. No. 17/235,071, mailing date Mar. 15, 2023, 7 Pages.
Notice of Allowance received for U.S. Appl. No. 17/235,071, mailing date Mar. 23, 2023, 2 Pages.
Office Action received for Japanese Patent Application No. 2021-078686, mailing date Jul. 12, 2022, 12 Pages (8 Pages of English Translation & 4 Pages of Official Copy).
Office Action received for Japanese Patent Application No. 2021-078686 mailing date Apr. 4, 2023, 3 Pages (1 Page of English Translation & 2 Pages of Official copy).
Office Action received for Japanese Patent Application No. 2021-078686 mailing date Apr. 4, 2023, 4 Pages (2 Pages of English translation & 2 Pages of official copy).
AACC, "The Definition of Dietary Fiber", AACC Report, Cereal Foods World, vol. 46, Jan. 10, 2001, pp. 112-129.

(56) References Cited

OTHER PUBLICATIONS

Aalto et al., "Dietary fiber content of barley grown in Finland", Cereal Chemistry, vol. 65, No. 4, 1988, pp. 284-286.
Aaman et al., "Analysis of total and insoluble mixed-linked (1→3),(1→4)-β-D-glucans in barley and oats", Journal of Agricultural and Food Chemistry, vol. 35, 1987, pp. 704-709.
Ajithkumar et al., "Isolation of cellotriosyl blocks from barley β-glucan with endo-1,4-β-glucanase from Trichoderma reesei", Carbohydrate Polymers, May 11, 2006, pp. 233-238.
Aman, P., "Analytical methods for the quantitative determination of mixed-linkage (1→3),(1→4)-β-D-glucans", In Book: Metabolic and physiological aspects of dietary fibre in food. Recent progress in the analysis of dietary fibre, 1995, pp. 153-159.
Aman et al., "Chemical composition of some different types of barley grown in Montana, U.S.A.", Journal of Cereal Science, vol. 4, No. 2, 1986, pp. 133-141.
Aman et al., "Molecular weight distribution of β-glucan in oat-based foods", Cereal Chemistry, vol. 81, No. 3, 2004, pp. 356-360.
Andersson, "Molecular weight and structure units of (1→3, 1→4)-β-glucans in dough and bread made from hull-less barley milling fractions", Journal of Cereal Science, vol. 40, No. 3, 2004, pp. 195-204.
Arentoft et al., "Determination of oligosaccharides by capillary electrophoresis", Journal of Chromatography A, vol. 652, Issue 2,, Oct. 22, 1993, pp. 517-524.
Asp, "Rapid enzymatic assay of insoluble and soluble dietary fiber", Journal of Agricultural and Food Chemistry, vol. 31, No. 3, 1983, pp. 476-482.
Aspinall, G. O., "Chemical characterization and structure determination of polysaccharides", The Polysaccharides, Academic Press, vol. 1, 1982, pp. 36-131.
Aspinall et al., "Structural investigations on the non-starchy polysaccharides of oat bran", Carbohydrate Polymers, vol. 4, No. 4, 1984, pp. 271-282.
Autio, K., "Functional aspects of cereal cell wall polysaccharides", Carbo-hydrates in food, 1996, pp. 227-264.
Bamforth et al., "Barley β-glucans. Their role in malting and brewing", Brewers Digest, vol. 35, 1982, pp. 22-27.
Barbosa et al., "Structural characterization of Botryosphaeran: a (1→3;1→6)-β-d-glucan produced by the ascomyceteous fungus, *Botryosphaeria* sp.", Carbohydrate Research, vol. 338, No. 16, Jul. 29, 2003, pp. 1691-1698.
Beer et al., "Effect of cooking and storage on the amount and molecular weight of (1→3), (1→4)-D-β-glucan extracted form oat products by an in vitro digestion system", Cereal Chemistry, vol. 74, No. 6, 1997, pp. 705-709.
Beer et al., "Extraction of Oat Gum from Oat Bran: Effects of Process on Yield, Molecular Weight Distribution, Viscosity and (1->3)(1-4)-β-D-Glucan Content of the Gum", Cereal Chemistry vol. 73, No. 1, 1996, pp. 58-62.
Beer et al., "Molecular weight distribution and (1→3),(1→4)-D-β-glucan content of consecutive extracts of various oat and barley cultivars", Cereal Chemistry, vol. 74, No. 4, 1997, pp. 476-480.
Bengtsson et al., "Isolation and chemical characterization of water-soluble arabinoxylans in rye grain", Carbohydrate Polymers, vol. 12, Issue 3, 1990, pp. 267-277.
Bhatty , "Laboratory and pilot plant extraction and purification of β-glucans from hull-less barley and oat brans", 1995, pp. 163-170.
Bhatty, "Total and extractable β-glucan contents of oats and their relationship to viscosity", Journal of Cereal Science, vol. 15, No. 2, 1992, pp. 185-192.
Biermann, Christopherj. , "Hydrolysis and other cleavages of glycosidic linkages in polysaccharides", Advances in Carbohydrate Chemistry and Biochemistry, vol. 46, 1988, pp. 251-271.
Bilad et al., "Membrane technology in microalgae cultivation and harvesting: A Review", Biotechnology Advances, vol. 32, 2014, pp. 1283-1300.
Blakeney et al., "A simple and rapid preparation of alditol acetates for monosaccharide analysis", Carbohydrate Research, vol. 113, No. 2, Mar. 1, 1983, pp. 291-299.

Bock et al., "Assignment of structures to oligosaccharides produced by enzymic degradation of a β-D-glucan from barley by 1H- and 13C-n.m.r. spectroscopy", Carbohydrate Research, vol. 211, No. 2, Apr. 24, 1991, pp. 219-233.
Bohm et al., "Rheological studies of barley (1→3),(1→4)-β-glucan in concentrated solution: investigation of the viscoelastic flow behaviour in the sol-state", Carbohydrate Research, vol. 315, Feb. 28, 1999, pp. 293-301.
Bohm et al., "Rheological studies of barley (1→3),(1→4)-β-glucan in concentrated solution: mechanistic and kinetic investigation of the gel formation", Carbohydrate Research, vol. 315, Feb. 28, 1999, pp. 302-311.
Bourdon et al., "Postprandial lipid, glucose, insulin and cholecystokinin responses in men fed barley pasta enriched with β-glucan", The American Journal of Clinical Nutrition, vol. 69, No. 1, Jan. 1, 1999, pp. 55-63.
Bowles et al., "13 C CP/MAS NMR study of the interaction of bile acids with barley β-D-glucan", Carbohydrate Polymers, vol. 29, No. 1, 1996, pp. 7-10.
Braaten et al., "Oat β-glucan reduces blood cholesterol concentration in hypercholesterolemic subjects", European Journal of Clinical Nutrition, Jul. 1, 1994, pp. 465-474.
Brown et al., "Cholesterol-lowering effects of dietary fiber: a meta-analysis", The American Journal of Clinical Nutrition, vol. 69, No. 1, Jan. 1, 1999, pp. 30-42.
Brown et al., "Immune recognition: A new receptor for β-glucans", Nature, 413, Sep. 6, 2001, pp. 36-37.
Buckeridge et al., "Mixed linkage (1→3),(1→4)-β-glucans of grasses", Cereal Chemistry, vol. 81, No. 1, 2004, pp. 115-127.
Buliga et al., "The sequence statistics and solution conformation of a barley (1→3),(1→4)-β-glucan", Carbohydrate Research, vol. 157, Dec. 1, 1986, pp. 139-156.
Burchard, Walther, "Structure formation by polysaccharides in concentrated solution", American Chemical Society, Biomacromolecules, vol. 2, Apr. 20, 2001, pp. 342-353.
Carr et al., "Enzymic determination of β-glucan in cereal-based food products", Cereal Chemistry, vol. 67, 1990, pp. 226-229.
Cavallero et al., "High (1→3,1→4)-β-glucan barley fractions in bread making and their effects on human glycemic response", Journal of Cereal Science, vol. 36, Issue 1, 2002, pp. 59-66.
Charlton et al., "Characterisation of a generic monoclonal antibody harvesting system for adsorption of DNA by depth filters and various membranes", Bioseparation, vol. 8, No. 6, 1999, pp. 281-291.
Cheng et al., "Improved analysis of dissolved carbohydrates in stream water with HPLC-PAD", Analytical Chemistry, vol. 73, 2001, pp. 458-461.
Chiesa et al., "Capillary zone electrophoresis of malto-oligosaccharides derivatized with 8-aminonaphthalene-1,3,6-trisulfonic acid", Journal of Chromatography A, vol. 645, No. 2, Aug. 20, 1993, pp. 337-352.
Claye et al., "Extraction and fractionation of insoluble fiber from five fiber sources", Food Chemistry, vol. 57, 1996, pp. 305-310.
Office Action received for Korean Patent Application No. 10-2021-7033983 mailing date Jun. 29, 2023, 13 Pages (6 Pages of English Translation and 7 Pages of Official Copy).
Notice of Allowance received for U.S. Appl. No. 17/235,071, mailing date Jun. 26, 2023, 2 Pages.
Colleoni-Sirghie et al., "Rheological and molecular properties of water soluble (1,3),(1,4)-D-β-glucans from high-β-glucan and traditional oat lines", Carbohydrate Polymers, vol. 52, No. 4, Jun. 1, 2003, pp. 439-447.
Colleoni-Sirghie et al., "Structural features of water soluble (1,3) (1,4)-β-d-glucans from high-β-glucan and traditional oat lines", Carbohydrate Polymers, vol. 54, No. 2, Nov. 1, 2003, pp. 237-249.
Cui et al., "Physicochemical properties and structural characterization by two-dimensional NMR spectroscopy of wheat β-D-glucan—comparison with other cereal β-D-glucans", Carbohydrate Polymers, vol. 41, No. 3, 2000, pp. 249-258.
Dais et al., "High-field, 13C-N.M.R. spectroscopy of β-d-glucans, amylopectin, and glycogen", Carbohydrate Research, vol. 100, Issue 1, 1982, pp. 103-116.

(56) References Cited

OTHER PUBLICATIONS

Davies et al., "Molecular ordering of cellulose after extraction of polysaccharides from primary cell walls of *Arabidopsis thaliana*: a solid-state CP/MAS 13C NMR study", Carbohydrate Research, vol. 337, Issue 7, Apr. 2, 2002, pp. 587-593.
Dawkins N. L., "Studies on the Extractability, Structural and Physicochemical Properties of Oat Gum/beta-glucan", Agriculture, Food Science And Technology, 1995, p. 1.
Degutyte-Fomins et al., "Oat Bran Fermentation by Rye Sourdough", Cereal Chemistry, vol. 79, No. 3, 2002, pp. 345-348.
Doublier et al., "Rheological properties of aqueous solutions of (1→3),(1→4)-β-D-glucan from oats", Cereal Chemistry, vol. 72, No. 4, 1995, pp. 335-340.
Drzikova et al., "The composition of dietary fibre-rich extrudates from oat affects bile acid binding and fermentation in vitro", Food Chemistry, vol. 90, No. 1-2, 2005, pp. 181-192.
Dudley et al., "High-resolution 13C CP/MAS NMR spectra solid cellulose oligomers and the structure of cellulose II", Journal of the American Chemical Society, vol. 105, 1983, pp. 2469-2472.
Edwards et al., "Plant cell wall polysaccharides, gums and hydrocolloids: Nutritional Aspects", In Book: Carbohydrates in food, 1996, pp. 319-345.
Ensley et al., "NMR spectral analysis of a water-insoluble (1→3)-β-D-glucan isolated from *Saccharomyces cerevisiae*", Carbohydrate Research, vol. 258, 1994, pp. 307-311.
Ferry, J. D., "Viscoelastic properties of polymers", vol. 8, No. 8, 1970, pp. 177-208.
Fincher et al., "Cell walls and their components in cereal grain technology", Advances in Cereal Science and Technology, 1986, pp. 207-295.
Finkelman et al., "(1→3)-ß-D-Glucan: Pharmaceutical Contaminant and Biological Response Modifier", Published by American Pharmaceutical Review,, 2016, pp. 16-19.
Forrest et al., "The Mode Of Binding Of B-glucans And Pentosans In Barley Endosperm Cell Walls", Journal of the Institute of Brewing, vol. 83, 1977, pp. 279-286.
Fulcher et al., "Structure of oat bran and distribution of dietary fiber components", Oat Bran, 1993, pp. 83-112.
Gefroh et al., "Multipronged Approach to Managing Beta-Glucan Contaminants in the Downstream Process: Control of Raw Materials and Filtration with Charge-Modified Nylon 6,6 Membrane Filters", American Institute of Chemical Engineers, Biotechnol. Prog., vol. 29, No. 3, Apr. 18, 2013, pp. 672-680.
Gomez et al., "Physical And Structural Properties Of Barley (1 → 3),(1 → 4)-β-D-glucan. Part II. Viscosity, Chain Stiffness And Macromolecular Dimensions", Carbohydrate Polymers, vol. 32, No. 1, 1997, pp. 17-22.
Gomez et al., "Physical and structural properties of barley (1 → 3),(1 →4)-β-d-glucan. Part I. Determination of molecular weight and macromolecular radius by light scattering", Carbohydrate Polymers, vol. 32, No. 1, 1997, pp. 7-15.
Gomez et al., "Physical and structural properties of barley (1→3),(1→4)-β-Dglucan—III. Formation of aggregates analysed through its viscoelastic and flow behaviour", Carbohydrate Polymers, vol. 34, No. 3, Dec. 20, 1997, pp. 141-148.
Grimm et al., "Solution properties of β-D-(1,3),(1,4)-glucan isolated from beer", Carbohydrate Polymers, vol. 27, No. 3, 1995, pp. 205-214.
Gruppen et al., "On the Large-Scale Isolation of Water-Insoluble Cell Wall Material from Wheat Flour", Cereal Chemistry, 1990, pp. 512-514.
Gruppen et al., "Water-unextractable cell wall material from wheat flour. 1. Extraction of polymers with alkali", Journal of Cereal Science, vol. 16, No. 1, 1992, pp. 41-51.
Guillon et al., "Structural and physical properties of dietary fibres, and consequences of processing on human physiology", Food Research International, vol. 33, 2000, pp. 233-245.
Gutierrez et al., "Structural characterization of extracellular polysaccharides produced by fungi from the genus *Pleurotus*", Carbohydrate Research, vol. 281, No. 1, Feb. 7, 1996, pp. 143-154.

Harding et al., "Molecular weight determination of polysaccharides", Advances in Carbohydrate Analysis, vol. 1, 1991, pp. 63-144.
Heims et al., "Determination of structural features of the water-insoluble dietary fiber from oats by the reductive-cleavage method", Carbohydrate Polymers, vol. 15, 1991, pp. 207-214.
Henry R. J., "Pentosan and (1 → 3), (1 → 4)-β-Glucan concentrations in endosperm and wholegrain of wheat, barley, oats and rye", Journal of Cereal Science, vol. 6, 1987, pp. 253-258.
Hofstetter-Kuhn et al., "Influence of borate complexation on the electrophoretic behavior of carbohydrates in capillary electrophoresis", Analytical Chemistry, vol. 63, 1991, pp. 1541-1547.
Houben et al., "Determination of the Pentosan Content of Wheat Products by Hydrolysis, Glucose Oxidase Treatment and Analysis by HPAEC/PAD", Journal of Cereal Science, vol. 26, No. 1, 1997, pp. 37-46.
Hromádková et al., "Influence of the drying method on the physical properties and immunomodulatory activity of the particulate (1→3)-β-d-glucan from *Saccharomyces cerevisiae*", Carbohydrate Polymers, vol. 51, No. 1, Jan. 1, 2003, pp. 9-15.
Huber et al., "HPLC of carbohydrates with cation-and anion-exchange silica and resin-based stationary phases", Journal of Chromatography Library, vol. 58, 1995, pp. 147-180.
Izydorczyk et al., "Structure And Physicochemical Properties Of Barley Non-starch Polysaccharides—I. Water-extractable B-glucans And Arabinoxylans", Carbohydrate Polymers, vol. 35, 1998, pp. 249-258.
Izydorczyk et al., "Structure And Physicochemical Properties Of Barley Non-starch Polysaccharides—ii. Alkaliextractable B-glucans And Arabinoxylans", Carbohydrate Polymers, vol. 35, No. 3-4, 1998, pp. 259-269.
Jaskari et al., "Effect of Hydrothermal and Enzymic Treatments on the Viscous Behavior of Dry- and Wet-Milled Oat Brans", Cereal Chemistry, vol. 72, No. 6, 1995, pp. 625-631.
Jenkins et al., "Dietary Fibre, Carbohydrate Metabolism And Chronic Disease", Advanced Dietary Fibre Technology, 2001, pp. 162-167.
Jiang et al., "Maldi-MS and Hplc Quantification Of Oligosaccharides Of Lichenase-hydrolyzed Water-soluble B-glucan From Ten Barley Varieties", Journal of Agricultural and Food Chemistry, vol. 48, 2000, pp. 3305-3310.
Johansen et al., "Molecular Weight Changes in the (1->3)(1->4)-beta-D-Glucan of Oats Incurred by the Digestive Processes in the Upper Gastrointestinal Tract of Pigs", Journal of Agricultural and Food Chemistry, vol. 41, 1993, pp. 2347-2352.
Johansen et al., "Physico-Chemical Properties and the Degradation of Oat Bran Polysaccharides in the Gut of Pigs", Journal of the Science of Food and Agriculture, vol. 73, 1997, pp. 81-92.
Johansson et al., "Comparison of the solution properties of (1→3),(1→4)-β-D-glucans extracted from oats and barley", Food Science and Technology, vol. 41, Issue 1, 2008, pp. 180-184.
Johansson et al., "Effect of Processing on the extractability of oat β-glucan", Food Chemistry, vol. 105, 2007, pp. 1439-1445.
Johansson et al., "Hydrolysis of β-glucan", Food Chemistry, vol. 97, Issue 1, 2006, pp. 71-79.
Johansson, Liisa, "Structural Analyses of (1→3),(1→4)-β-D-Glucan of Oats and Barley", Department of Applied Chemistry and Microbiology, Apr. 7, 2006, 85 pages.
Johansson et al., "Structural analysis of water-soluble and -insoluble β-glucans of whole-grain oats and barley", Carbohydrate Polymers, vol. 58, Issue. 3, 2004, pp. 267-274.
Johansson et al., "Structural characterization of water soluble β-glucan of oat bran", Carbohydrate Polymers, vol. 42, 2000, pp. 143-148.
Johnson et al., "Formation of sucrose pyrolysis products", Journal of Agricultural and Food Chemistry, vol. 17, 1969, pp. 22-24.
Johnson et al., "Pulsed electrochemical detection of carbohydrates at gold electrodes following liquid chromatographic separation", Journal of Chromatography Library, vol. 58, 1995, pp. 391-429.
Kaar et al., "The Complete Analysis of Wood Polysaccharides Using HPLC", Journal of Wood Chemistry and Technology, vol. 11, 1991, pp. 447-463.

(56) References Cited

OTHER PUBLICATIONS

Kabay et al., "Removal of boron from aqueous solutions by a hybrid ion exchange—membrane process", vol. 198, Issue 1-3, Oct. 30, 2006, pp. 158-165.

* cited by examiner

Contour Plots of Beta Glucan: Intermediate Hold

FIG. 11 Contour Plots of Beta Glucan: High Hold

REDUCTION OF LEACHABLE BETA-GLUCAN LEVELS FROM CELLULOSE-CONTAINING FILTER MATERIALS

CROSS-REFERENCE TO RELATED APPLICATIONS

The present application is a Continuation Application of U.S. application Ser. No. 17/235,071, filed Apr. 20, 2021, which is a Continuation Application of U.S. application Ser. No. 16/316,890, filed Jan. 10, 2019, now U.S. Pat. No. 11,014,031, which is a US National Stage Application of International Application No. PCT/US2017/057878, filed Oct. 23, 2017, which claims the benefit of priority of U.S. Provisional Patent Application No. 62/413,013, filed Oct. 26, 2016, each of which is incorporated by reference herein in its entirety.

FIELD OF THE DISCLOSURE

The present disclosure generally relates to the reduction of the level of (1→3)-β-D-glucan leachables from cellulose-containing filter materials.

BACKGROUND OF THE DISCLOSURE

Cellulose-containing media and filters are widely used in biopharmaceutical and plasma purification processes for removal of impurities from target molecules. (1→3)-β-D-glucan ("beta-glucans") is an inherent impurity in the cellulosic matrix and can leach out into the product stream during the filtration of proteins and similar components. Regulatory agencies require biopharmaceutical manufacturers to closely monitor levels of beta-glucan impurities and maintain them below a defined threshold. Elevated levels of beta-glucan leachables originating from filters, particularly ones being used further downstream in the process, are a cause of concern due to patient safety and regulatory reasons. In addition, serum-based product manufacturers are required to maintain beta-glucan leachable levels below threshold amounts.

SUMMARY OF THE DISCLOSURE

Among the various aspects of the present disclosure is the provision of a method for reducing the amount of leachable beta-glucans in a cellulose-containing filter material.

Briefly, therefore, the present disclosure is directed to a method for reducing the amount of leachable beta-glucans in a cellulose-containing filter material, the method comprising treating the filter material with a solution comprising a carbonate salt, an organic carbonate (such as a carbonate ester), or carbonic acid.

Another aspect of the disclosure is the provision of a cellulose-containing filter material treated in accordance with the methods described herein, wherein the filter material has a reduced amount of leachable beta-glucans as compared to an untreated filter material.

Another aspect of the disclosure is the provision of a method for preparing a biopharmaceutical or a plasma derivative having a reduced amount of leached beta-glucan, the method comprising treating the biopharmaceutical or a plasma derivative by contact with a cellulose-containing filter material treated in accordance with the methods described herein.

Another aspect of the disclosure is the provision of a biopharmaceutical or a plasma derivative prepared by contacting the same with a cellulose-containing filter material treated in accordance with the methods described herein, wherein the biopharmaceutical or a plasma derivative comprises a reduced amount of leached beta-glucans as compared to an untreated biopharmaceutical or a plasma derivative.

Other objects and features will be in part apparent and in part pointed out hereinafter.

BRIEF DESCRIPTION OF THE DRAWINGS

These and other features, aspects, and advantages of the disclosure will become more fully apparent from the following detailed description, appended claims, and accompanying drawings, wherein the drawings illustrate features in accordance with exemplary aspects of the disclosure, and wherein:

ABBREVIATIONS AND DEFINITIONS

Figure 1:
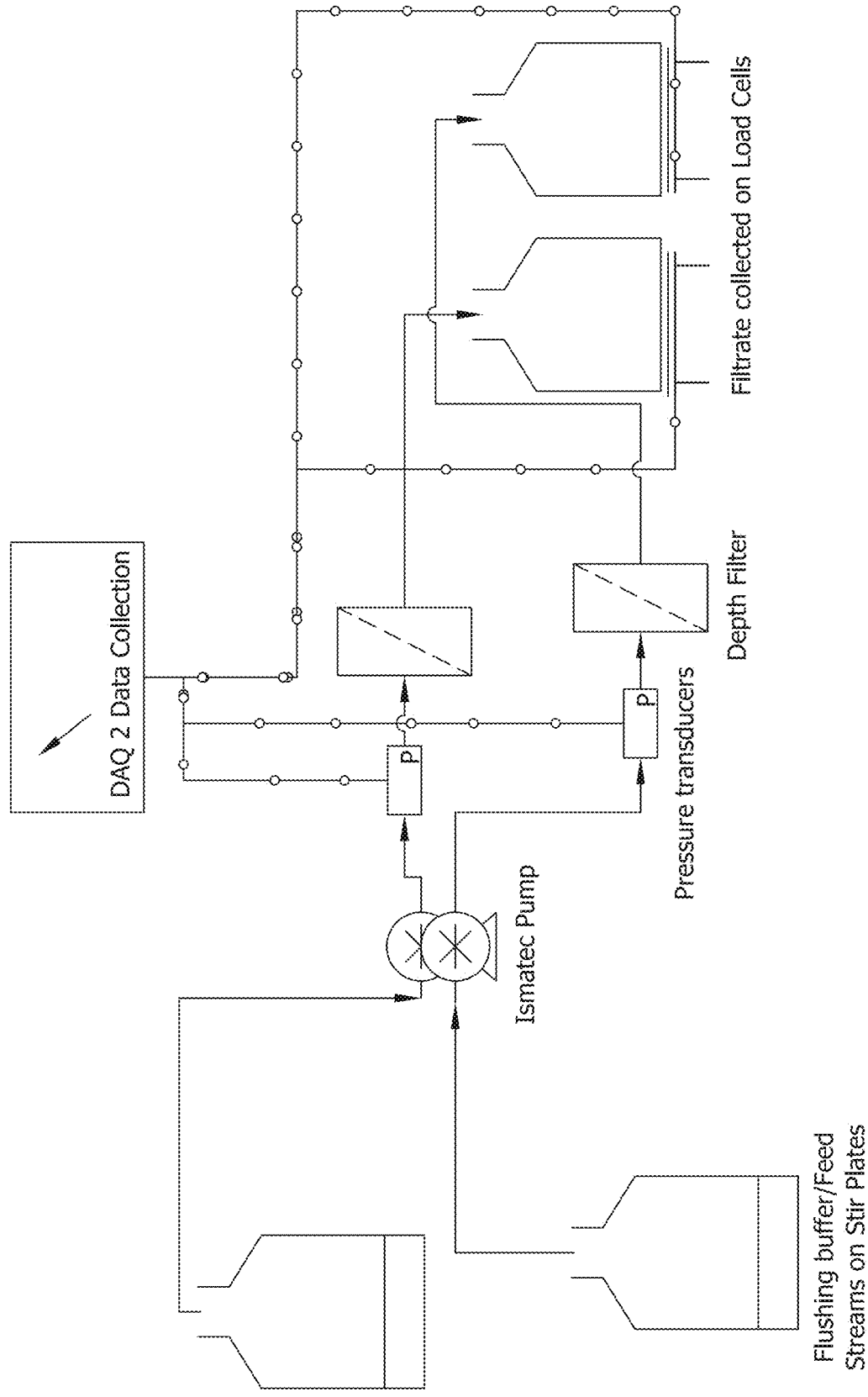
FIG. 1 is an exemplary schematic of bench scale setup for investigation of specialized flushes.

The following definitions and methods are provided to better define the present disclosure and to guide those of ordinary skill in the art in the practice of the present disclosure. Unless otherwise noted, terms are to be understood according to conventional usage by those of ordinary skill in the relevant art.

All publications, patents and patent applications cited herein, whether supra or infra, are hereby incorporated by reference in their entirety to the same extent as if each individual publication, patent or patent application was specifically and individually indicated to be incorporated by reference.

The term "comprising," which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "component" includes one, two or more such components.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

DETAILED DESCRIPTION OF THE DISCLOSURE

One aspect of the present disclosure is directed to a method for reducing the amount of leachable beta-glucans in a cellulose-containing filter material. It has been advantageously discovered that the methods described herein, and treated filter materials produced thereby, can significantly reduce the amount of beta-glucans that commonly leach into a product pool (i.e., the components collected following a filtration pass) such as a biopharmaceutical or plasma derivative.

In general, the methods and filters described herein are capable of reducing the level of leachable beta-glucans in a cellulose-containing filter material by greater than 10%, greater than 20%, greater than 30%, greater than 40%, greater than 50%, greater than 60%, greater than 70%, greater than 80%, greater than 90%, greater than 95%, or greater than 99%. Such leached beta-glucans can be detected, for example, in the filtrate following the treatment process (i.e., as an indicator of treatment efficacy). Where treated cellulose-containing filter materials described herein are subsequently employed in biopharmaceutical or plasma derivative processing, this reduction in leachable beta-glucan levels may translate, for example, to a biopharmaceutical or plasma derivative product having a beta-glucan impurity level of less than 1000 pg/ml, less than 900 pg/ml, less than 800 pg/ml, less than 700 pg/ml, less than 600 pg/ml, less than 500 pg/ml, less than 400 pg/ml, less than 300 pg/ml, less than 200 pg/ml, or less than 100 pg/ml. The lower limit of beta-glucan impurities is not particularly limited, and may preferably be less than 50 pg/ml or even less.

Treatment Solution

The methods described herein involve treating a cellulose-containing filter material with a carbonate-containing solution. In general, treatment of the filter material is carried out by soaking, circulating, recirculating, washing, flushing, passing through, or otherwise contacting the filter material with the solution in order to remove leachable beta-glucans therefrom, as discussed in further detail below.

The carbonate-containing solution includes a carbonate salt, an organic carbonate, or carbonic acid. Combinations of carbonate salts, organic carbonates, and/or carbonic acid may also be employed.

In some embodiments, for example, the solution includes a carbonate salt. Exemplary carbonate salts include ammonium carbonate, ammonium hydrogen carbonate, barium carbonate, calcium carbonate, iron carbonate, lithium carbonate, magnesium carbonate, manganese carbonate, potassium carbonate, potassium hydrogen carbonate, sodium carbonate, sodium hydrogen carbonate, and mixtures thereof. In one particular embodiment, the carbonate salt is selected from the group consisting of ammonium carbonate, calcium carbonate, iron carbonate, magnesium carbonate, manganese carbonate, potassium carbonate, sodium carbonate, and mixtures thereof. In another particular embodiment, the carbonate salt is selected from the group consisting of ammonium carbonate, calcium carbonate, potassium carbonate, sodium carbonate, and mixtures thereof. In one preferred embodiment, the carbonate salt is sodium carbonate, potassium carbonate, or a mixture thereof.

In other embodiments, for example, the solution includes an organic carbonate. The organic carbonates generally have the formula: $RO[(CO)O]_nR$, wherein each R is independently a substituted or unsubstituted, straight-chain or branched aliphatic, aromatic/aliphatic (araliphatic) or aromatic hydrocarbon radical having 1 to 20 C atoms. The two radicals R may also be joined to one another to form a ring. The two radicals R may be the same or different; in one particular embodiment they are the same. In this embodiment, R is preferably an aliphatic hydrocarbon radical and more preferably a straight-chain or branched alkyl radical having 1 to 5 C atoms, or a substituted or unsubstituted phenyl radical. R in this case is a straight-chain or branched, preferably straight-chain (cyclo)aliphatic, aromatic/aliphatic or aromatic, preferably (cyclo)aliphatic or aromatic, more preferably aliphatic hydrocarbon radical having 1 to 20 C atoms, preferably 1 to 12, more preferably 1 to 6, and very preferably 1 to 4 carbon atoms. Examples of such radicals are methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, o- or p-tolyl or naphthyl. These radicals R may be the same or different; they are preferably the same. The radicals R may also be joined to one another to form a ring. Examples of divalent radicals R of this kind are 1,2-ethylene, 1,2-propylene, and 1,3-propylene. Generally speaking, n is an integer from 1 to 5, preferably from 1 to 3, more preferably from 1 to 2. The carbonates may preferably be simple carbonates of the general formula RO(CO)OR, i.e., n in this case is 1.

Examples of suitable carbonates comprise aliphatic, aromatic/aliphatic or aromatic carbonates such as ethylene carbonate, 1,2- or 1,3-propylene carbonate, diphenyl carbonate, ditolyl carbonate, dixylyl carbonate, dinaphthyl carbonate, ethyl phenyl carbonate, dibenzyl carbonate, dimethyl carbonate, diethyl carbonate, di-n-propyl carbonate, di-n-butyl carbonate, diisobutyl carbonate, dipentyl carbonate, dihexyl carbonate, dicyclohexyl carbonate, diheptyl carbonate, dioctyl carbonate, didecyl carbonate or didodecyl carbonate. One exemplary substituted carbonate is glycerol carbonate. Examples of carbonates in which n is greater than 1 comprise dialkyl dicarbonates, such as di-tert-butyl dicarbonate, or dialkyl tricarbonates such as di-tert-butyl tricarbonate. One exemplary aromatic carbonate is diphenyl carbonate. In one particular embodiment, the organic carbonate is a carbonate ester is selected from the group consisting of dimethyl carbonate, diphenyl carbonate, ethylene carbonate, trimethylene carbonate, propylene carbonate, glycerol carbonate, and mixtures thereof.

The pH of the carbonate-containing solution generally ranges from about 7.5 to about 12 (e.g., about 7.5, about 8, about 8.5, about 9, about 9.5, about 10, about 10.5, about 11, about 11.5, or about 12). In one embodiment, for example, the pH of the solution ranges from about 8.5 to about 12 (e.g., about 8.5, about 8.75, about 9, about 9.25, about 9.5, about 9.75, about 10, about 10.25, about 10.5, about 10.75, about 11, about 11.25, about 11.5, about 11.75, or about 12). In one preferred embodiment, the pH of the solution ranges from about 10 to about 12 (e.g., about 10.1, about 10.2, about 10.3, about 10.4, about 10.5, about 10.6, about 10.7, about 10.8, about 10.9, about 11, about 11.1, about 11.2, about 11.3, about 11.4, about 11.5, about 11.6, about 11.7, about 11.8, about 11.9, or about 12).

The carbonate concentration of the solution may vary depending, for example, upon the carbonate chosen (e.g., a carbonate salt or carbonic acid) the desired pH, and/or the hold time of the treatment process. In one embodiment, for example, the carbonate concentration may have a lower limit of about 0.005 mM and an upper limit of the maximum solubility limit of the particular carbonate employed. In another embodiment, the carbonate concentration of the solution is from about 0.005 mM to about 2M. Thus, for example, the carbonate concentration may be about 0.005 mM, about 0.01 mM, about 0.025 mM, about 0.05 mM, about 0.1 mM, about 0.5 mM, about 1 mM, about 5 mM, about 10 mM, about 25 mM, about 50 mM, about 0.1 M, about 0.15 M, about 0.2 M, about 0.25 M, about 0.5 M, about 0.75 M, about 1.0 M, about 1.25 M, about 1.5 M, about 1.75 M, or about 2 M. In one particular embodiment, the carbonate concentration of the solution is from about 0.01 M to about 0.5 M. In another particular embodiment, the carbonate concentration of the solution is from about 0.01 M to about 1 M. In embodiments in which organic carbonate are employed, for example, they may be used as-is (i.e., without dilution or in aqueous forms).

In addition to the carbonate, the solution may contain a buffering agent in order to maintain the pH range within the desired range (e.g., to about 8.5 to about 12) and otherwise modulate the solution concentration. Any buffer can be used in the solutions provided herein so long as it does not adversely affect the carbonate component and supports the requisite pH range required. Exemplary buffering agents include sodium hydroxide, potassium hydroxide, and the like. In one particular embodiment, the buffering agent is sodium hydroxide. Typically, the buffering agent concentration will be 0.005 mM, about 0.01 mM, about 0.025 mM, about 0.05 mM, about 0.1 mM, about 0.5 mM, about 1 mM, about 5 mM, about 10 mM, about 25 mM, about 50 mM, about 0.1 M, about 0.15 M, about 0.2 M, about 0.25 M, about 0.5 M, about 0.75 M, about 1.0 M, about 1.25 M, about 1.5 M, about 1.75 M, or about 2 M. In some embodiments, and dependent upon the buffering agent(s) chosen, and the pH and concentration of the same, the buffering agent may provide a sanitizing benefit to the filter material.

As noted above, treatment of the filter material involves soaking, circulating, recirculating, washing, flushing, passing through, or otherwise contacting the filter material with the solution. In general, any conventional wash or flush method for preparing filter materials for use can be employed. Additionally, or alternatively, filter components such as cellulose pulp or membranes can be treated as described herein prior to fabrication of a device including the filter material. Thus, for example, the filter material may be treated or contacted with the solution for anywhere from 30 seconds to 6 hours, or longer, provided that the length of time does not adversely affect or impair the performance of the filter material.

In one embodiment, the filter material is soaked or immersed in the solution for a period of time (i.e., a static soak). Typically, for example, the filter material is soaked or immersed in the solution for about 1 minute to about 240 minutes (e.g., about 15 minutes, about 30 minutes, about 45 minutes, about 60 minutes, about 75 minutes, about 90 minutes about 105 minutes, about 120 minutes, about 135 minutes, about 150 minutes, about 165 minutes, about 180 minutes, about 195 minutes, about 210 minutes, about 225 minutes, or about 240 minutes). In one particular embodiment, the filter material is soaked or immersed in the solution for about one minute to about 180 minutes (e.g., about 15 minutes, about 30 minutes, about 45 minutes, about 60 minutes, about 75 minutes, about 90 minutes about 105 minutes, about 120 minutes, about 135 minutes, about 150 minutes, about 165 minutes, or about 180 minutes). In another particular embodiment, the filter material is soaked or immersed in the solution for about 60 minutes to about 120 minutes (e.g., about 60 minutes, about 75 minutes, about 90 minutes about 105 minutes, or about 120 minutes).

In another embodiment, the method includes recirculation of the solution through the filter material, e.g., two or more passes of the solution through the filter material via a pump system. An exemplary recirculation arrangement is described in Example 1 and FIG. 2. Use of conventional filtration, tangential flow filtration, and similar methods can be readily applied to recirculation embodiments described herein. For example, average system hold up in a depth filter train is on the order of about 10 L/m2 to about 100 L/m2. In one particular embodiment, the average system hold up is about 10 L/m2 to about 60 L/m2; for example, 25 L/m2 to about 60 L/m2.

It will be understood that the above pH, carbonate concentrations, and contact/circulation regimes can be optimized to provide maximum reduction of leachable beta-glucans (see, e.g., Example 2). For example, in certain cases higher pH (e.g., 10 to 12) and higher contact time (e.g., 80 to 120 minutes) at lower concentrations (e.g., 0.01 M to 0.5 M) can be particularly effective in reducing leached beta-glucan levels. By way of another example, lower pH (e.g., 7.5 to 10) may require higher molarities (e.g., 0.5 M to solubility limits) for most effective reduction of leachable beta-glucan levels. By way of yet another example, extended hold times (>80 minutes) can be particularly effective for reducing leached beta-glucans to under 100 pg/ml with pH 11-12 solution at less than 0.5 M carbonate concentration. By way of yet another example, lower pH (e.g., 7.5-10), higher carbonate concentrations (>0.8 M), and lower static hold times (e.g., 1-20 minutes) can be particularly effective in reducing leached beta-glucan levels. In one particular embodiment, the solution has a carbonate concentration of 0.01 M to 1 M, a pH of 10 to 12, and the filter material is immersed in a static soak for 100 to 120 minutes. In another particular embodiment, the solution has a carbonate concentration of 0.01 M to 0.5 M, a pH of 11 to 12, and the filter material is immersed in a static soak for 80 to 120 minutes.

The pressure of the treatment regime (e.g., in a pass or flow-through or (re)circulation arrangement) is not narrowly critical, provided that the pressures do not adversely affect or impair the performance of the filter material and/or removal of leachable beta-glucans.

Cellulose-Containing Filter Material

In general, the methods described herein for removing leachable beta-glucan described herein may be employed with any cellulose-containing filtration or solid support material, media, or membrane, which may pose a risk of leaching beta-glucans into a desired product. As described in further detail herein, the treatment can be carried out either before or after formation of a filtration device (e.g., including a housing for the filter material), both before and after formation of the filtration device, before filtration of a desired product (i.e., as a pre-treatment), and combinations and multiples thereof. Thus, another aspect of the present disclosure is a cellulose-containing filter material treated in accordance with the methods described herein, wherein the filter material has a reduced amount of leachable beta-glucans as compared to an untreated filter material.

As a cellulose-containing filter material, the filter material may include cellulose fibers (e.g., wood pulp and/or cotton derived), regenerated cellulose fibers, cellulose fibers combined with inorganic filter aids (e.g. diatomaceous earth, perlite, fumed silica), cellulose fibers combined with inorganic filter aids and organic resins, cellulose/silica blends, cellulose derivatives such as cellulose acetate or cellulose triacetate, or any combination thereof. These materials and their methods of making them either by a wet process (similar to papermaking) or a dry process are well known in the art.

In some embodiments, for example, the filter material is a depth filter or will be used to ultimately form a depth filter device. Representative commercially available depth filters which may be used in accordance with the treatment methods herein include, for example, 3M/CUNO AP series depth filters (AP01); 3M/CUNO CP series depth filters (CP10, CP30, CP50, CP60, CP70, CP90), 3M/CUNO HP series depth filters (HP10, HP30, HP50, HP60, HP70, HP90), 3M/CUNO CA series depth filters (CA10, CA30, CA50, CA60, CA70, CA90), 3M/CUNO SP series depth filters (Examples include SP10, SP30, SP50, SP60, SP70, SP90); 3M/CUNO Delipid and Delipid Plus filters; 3M/CUNO Polynet Filters (Polynet-PB); 3M/CUNO Life Assure filters; EMD Millipore CE series depth filters (CE15, CE20, CE25, CE30, CE35, CE40, CE45, CE50, CE70, CE75); EMD Millipore DE series depth filters (DE25, DE30, DE35, DE40, DE45, DE50, DE55, DE560, DE65, DE70, DE75); EMD Millipore HC filters (A1HC, B1HC, COHC, D0HC, X0HC, VPF, F0HC), Clarisolve (40MS, 20MS); EMD Millipore Corporation Clarigard®, Polygard®, Millistak+®, and Polysep® filters; ManCel Associates depth filters (PR 12 UP, PR12, PR 5 UP), and PALL Corporation filters (Bio20, SUPRA EKIP, KS-50P); Sartorius AG filters (Sartobran®); and the like.

In other embodiments, the filter material is a wood pulp.

Other filter materials and devices that can be treated in accordance with the methods described herein include absorbents, ultrafiltration membranes, dialyzers, and like materials containing cellulose or derivatives thereof. Again, such materials may be treated as described herein either before or after (or both before and after) formation of the commercial filtration device.

Biopharmaceuticals and Plasma Derivatives

As noted above, cellulose-containing media and filters are widely used in biopharmaceutical and plasma purification processes for removal of impurities from target molecules. Accordingly, another aspect of the present disclosure is a method for preparing a biopharmaceutical or a plasma derivative having a reduced amount of leached beta-glucan, the method comprising treating the biopharmaceutical or a plasma derivative by contact with a cellulose-containing filter material treated in accordance with any preceding method of treatment claim. Yet another aspect of the present disclosure is a biopharmaceutical or a plasma derivative prepared in accordance with the aforementioned method.

In general, conventional methods for preparing (i.e., filtering) biopharmaceutical or a plasma derivatives may be employed, except that standard filters and filter materials are replaced with the treated cellulose-containing filter materials described herein.

The biopharmaceutical or a plasma derivative that may be prepared/purified using the methods described herein is not narrowly critical; any suitable biopharmaceutical or a plasma derivative that is commonly filtered as described herein may be employed. By way of illustration, blood factors (e.g., Factor VIII and Factor IX), thrombolytic agents (e.g., tissue plasminogen activator), hormones (e.g., insulin, glucagon, growth hormone, gonadotrophins), haematopoietic growth factors (e.g., erythropoietin, colony stimulating factors), interferons (e.g., interferons-α, -β, -γ), interleukin-based products (e.g., interleukin-2), vaccines (e.g., hepatitis B surface antigen), monoclonal antibodies (many known examples), and other products (e.g., (tumor necrosis factor, therapeutic enzymes), and the like are contemplated.

Having provided the disclosure in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the subject matter disclosed herein, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1: Investigation of Different Flushing Chemistries for Removal of Beta-Glucan from Depth Filtration Media In this example five specialized flushing chemistries were tested for removal of beta-glucans from cellulosic depth media. The investigated chemistries included 2 M sodium chloride, 4 M urea, 1M sodium carbonate buffer pH 10, 0.5N sodium hydroxide and RODI water (Milli Q). Solutions were prepared and sterile filtered prior to use. Experiments were performed on Viresolve Pre Filter (VPF) micro devices with 5 $cm^2$ membrane area (OptiScale 40 Capsule Cat No SSPVA40NB9). Experimental setup included an automated data collection system (DAQ 2.0) for collecting pressure drop and flowrate data, platinum cured silicon tubing flow path (Cat No #HV-96410-14, Cole Parmer, IL, USA), single use pressure transducers (PDKT-104-03, Pendotech, NJ). Four trains were setup in parallel. Schematic of experimental setup is shown in FIG. 1.

The filter was flushed with 100 $L/m^2$ of specialized flush solution followed by static hold for 1 hr. At the end of hold time the filter was flushed with 400 $L/m^2$ of purified water at 600 LMH.

Post RODI flush the filter was equilibrated with 30 L/m² equilibration buffer (25 mM Tris pH 7). Post equilibration 30 L/m² of monoclonal antibody solution was loaded and the filtrate was collected into 15 ml polystyrene centrifuge tubes. These samples were analyzed for leached beta-glucan using a Charles River PTS Rapid Micro Method Glucan assay. The standard flush, which was used as a control, included 100 L/m² RODI flush followed by 30 L/m² Buffer equilibration. Table 1 summarizes the process. Flux for all steps was set at 360 L/m²·hr.

TABLE 1

Summary of flushing strategy

| Flush Solution | Flush Volume (L/m²) | Hold time (hrs.) | Standard Flush (L/m²) | | Protein solution (L/m²) |
| | | | RODI | Buffer 25 mM Tris pH 7 | |
| --- | --- | --- | --- | --- | --- |
| Control (Standard Flush) | 0 | 0 | 100 | 30 | 30 |
| Water (control) | 100 | 1 | 400 | 30 | 30 |
| 4M Urea | 100 | 1 | 400 | 30 | 30 |
| 2M Sodium Chloride | 100 | 1 | 400 | 30 | 30 |
| 1M Carbonate solution pH 10 | 100 | 1 | 400 | 30 | 30 |
| 0.5N Sodium Hydroxide | 100 | 1 | 400 | 30 | 30 |

Figure 2:
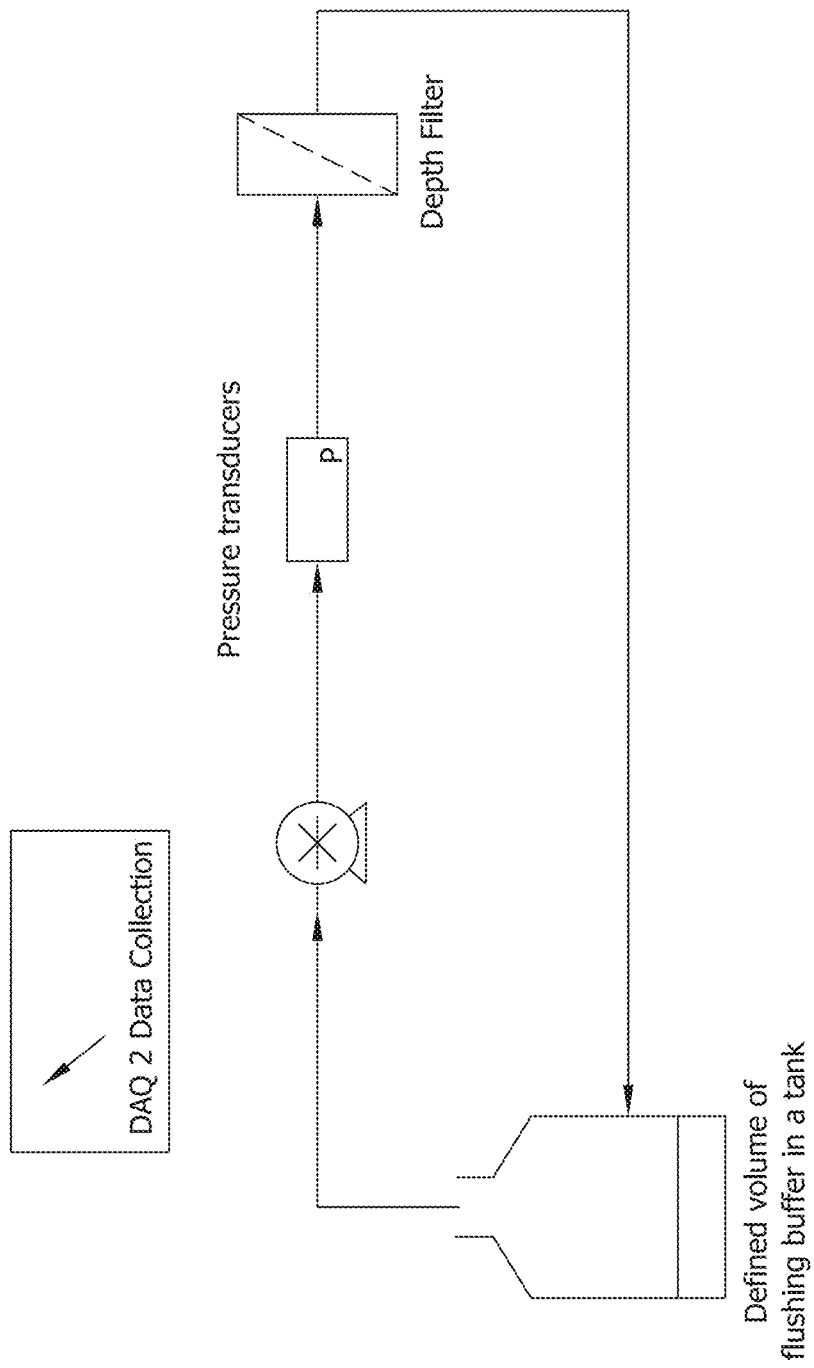
FIG. 2 is an exemplary schematic of bench scale setup for investigation of specialized flushes in recirculation mode.

Experimental setup for the recirculation mode is shown in FIG. 2. In recirculation mode, a defined amount of flushing buffer was dispensed in the feed tank. Outlet of the depth filter to be flushed was placed in the feed tank. Flushing was performed at a defined flowrate and for a defined time. Same equipment setup and filters as flow through mode were used for recirculation study described above, with the main difference being that the filter outlet was directed back to feed tank in recirculation mode. The three levels investigated include 25 L/m², 50 L/m² and 60 L/m². All three volume to area ratios reduced the leached beta glucan levels to 100-200 pg/ml range and were effective.

Figure 3:
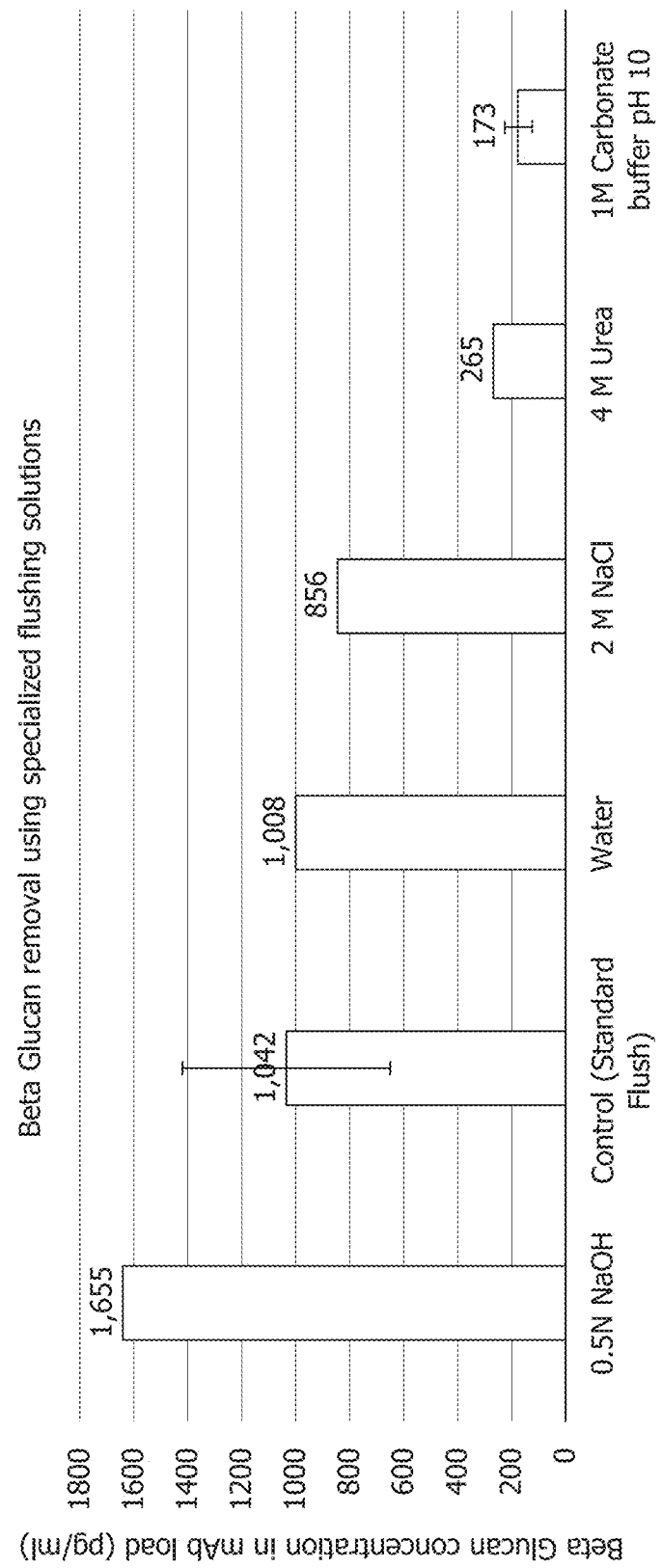
FIG. 3 is a graph illustrating an effect of specialized flushes on leached beta-glucan levels in a product pool.

Protein pools collected at a protein solution volume to filter area ratio of 30 L/m² were tested for beta-glucan levels. Confirmatory runs were performed using a second VPF lot. For both the lots, the reduction in beta-glucan leachables in the product pool was greater than 80% (compare light green bar (control, standard flush) with dark green (1 M carbonate flush)). The results are shown in FIG. 3.

Figure 4:
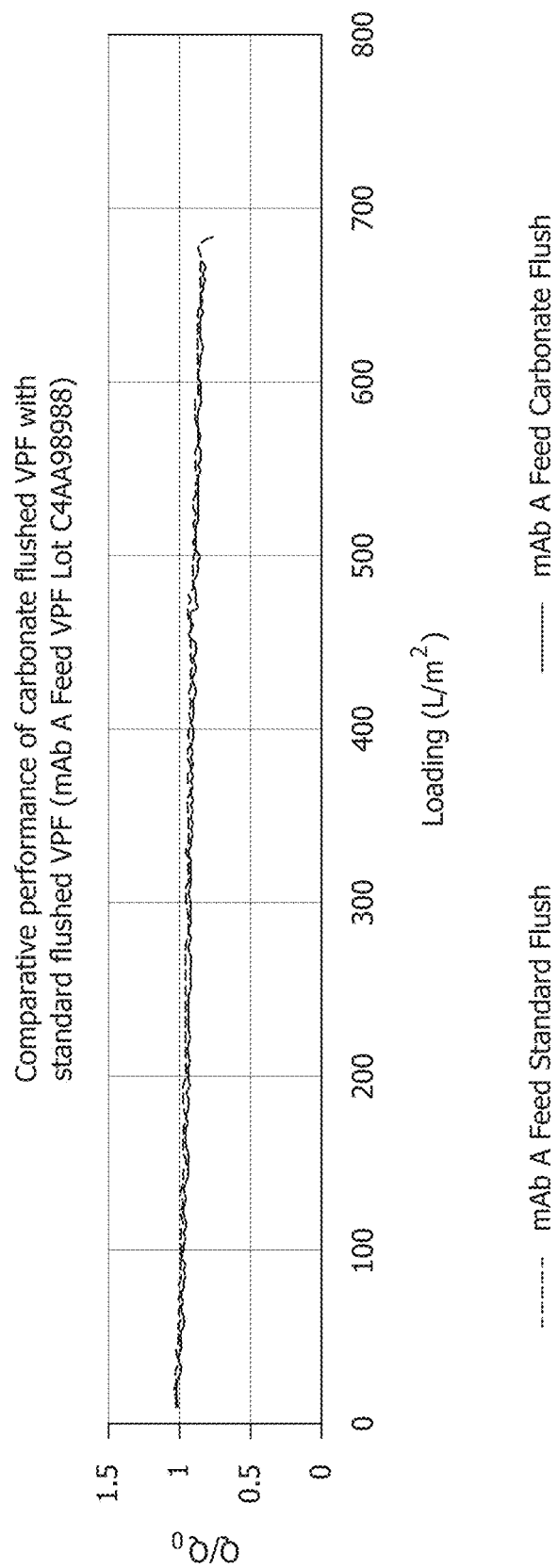
FIG. 4 is a graph illustrating VPro Comparative performance of carbonate flushed and standard flushed VPF (Monoclonal antibody A, VPF Lot C4AA98988).
Figure 5:
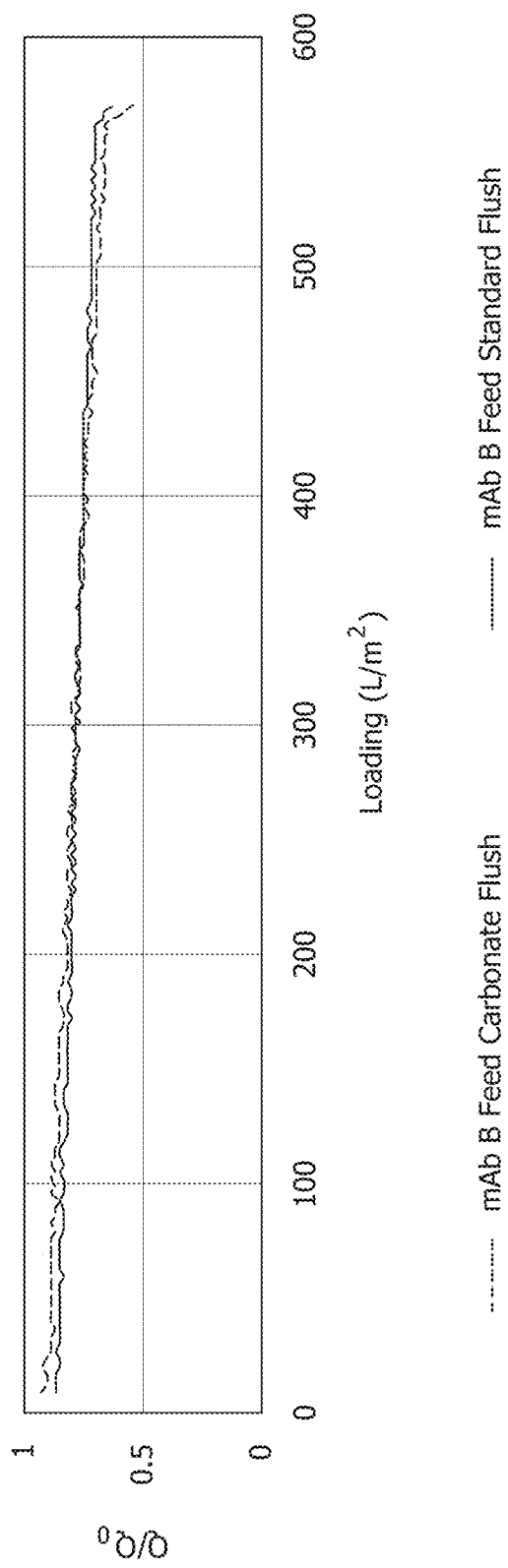
FIG. 5 is a graph illustrating VPro Comparative performance of carbonate flushed and standard flushed VPF (Monoclonal antibody B, VPF Lot C3AA43491).

To ensure that specialized flushing strategy using 1 M sodium carbonate pH 10 solution does not negatively affect Viresolve Pre Filter absorptive capacity was tested a comparative performance test was performed. Viresolve Pre Filter (VPF) Devices flushed with standard flush (control) and specialized flush were used as pre filters for Viresolve Pro Filters. Viresolve Pro flux profiles were compared to investigate any impact of the specialized flush on pre filter performance. This test was performed on two different lots of VPF and capacities were tested on two different monoclonal antibody feeds. No detrimental impact on VPF absorptive capacity was observed in either of the two cases. Results are shown in FIG. 4 and FIG. 5.

Example 2: Investigation of Specialized Flush Parameters on Beta-Glucan Removal Efficiency 1. Effect of Carbonate Counter Ion Analysis of carbonate counter ion was performed to evaluate operational feasibility of its usage as a flushing solution for beta-glucan removal. Primary criteria selected for the analysis were toxicity, solubility and other operational concerns. A summary of exemplary investigated counter ions is provided in Table 2.

TABLE 2

Analysis of counter ions

| Cation | Toxicity | Carbonate Solubility (gm per 100 gm water) |
| --- | --- | --- |
| Sodium($Na^+$) | Low (irritant) | 21.5 |
| Potassium ($K^+$) | Low | 111 |
| Calcium ($Ca^{2+}$) | Non toxic | $7.753 \times 10^{-4}$ (Argonite) |
| Carbonic acid | NA | NA |
| Ammonium ($NH_4^+$) | Irritant | 10 |
| Organic Carbonates | Non toxic/low toxicity | High |
| Magnesium ($Mg^{2+}$) | Non toxic | 0.039 |
| Manganese ($Mn^{2+}$) | Non toxic | $4.877 \times 10^{-5}$ |
| Iron ($Fe^{2+}$) | Not available | $6.554 \times 10^{-5}$ |
| Barium ($Ba^{2+}$) | Intermediate toxicity (2 on NFPA704) | $1.409 \times 10^{-3}$ |

As shown above sodium ($Na^+$) and potassium ($K^+$) are the most preferred counter ions based on toxicity, solubility and other operational concerns. Calcium in combination with carbonic acid can be used but have operational challenges associated to carbon dioxide sparging. Ammonium ($NH_4^+$) carbonate can be used for pump treatment but usage in GMP environment can be challenging as it is strong irritant. Organic carbonates can also be used. Other counter ions like magnesium, manganese, iron have limited solubility and barium carbonate is toxic as well as has low solubility. Experiments were performed to compare the sodium and potassium counter ions in removal of beta-glucans from depth filtration media.

Figure 6:
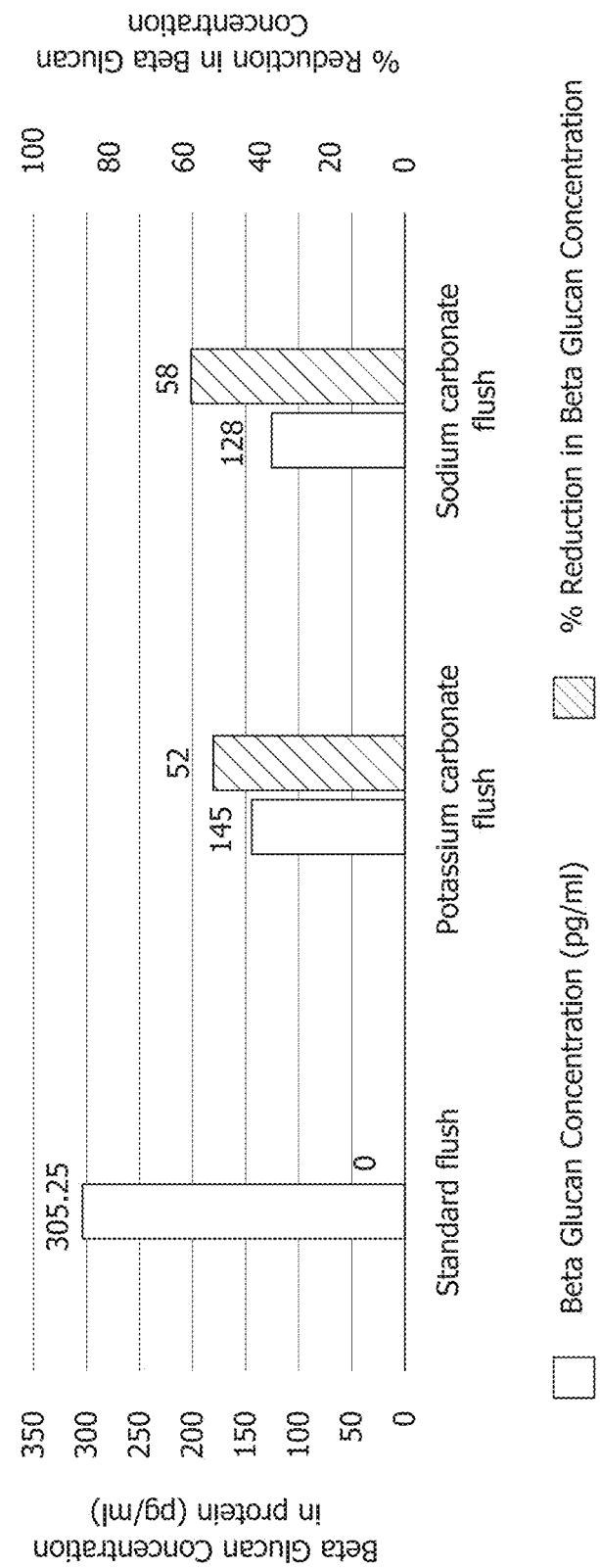
FIG. 6 is a graph illustrating a comparison of Sodium and Potassium carbonate for removal of beta-glucans from depth filters.

Experimental sodium and potassium carbonate were investigated for removal of beta-glucans from depth filter. In case of both sodium and potassium carbonate flushes 0.5 M concentration solution at pH 10 were used. 100 L/m² solution flush was performed at 200 LMH flux. No static hold was performed. After solution flush, 400 L/m² water flush was performed at 600 LMH. Filters were then conditioned with 50 mM acetate buffer 80 mM sodium chloride pH 5.5 buffer by flowing through 30 L/m² of buffer at 600 LMH. Post buffer flush 30 L/m² monoclonal antibody feed was loaded at 100 LMH as a model protein. This protein load was collected and analyzed for leached beta-glucans. Charles River PTS Rapid Micro Method Glucan assay was used for beta-glucan analysis. As shown in FIG. 6, both sodium and potassium carbonate showed comparable performance for removal of beta-glucans from depth media.

2. Effect of Solution Concentration, pH and Static Hold Time

A design of experiment (DOE) was performed to identify effective range for pH, concentration and static hold time. A Box Behnken design was selected for the study. List of parameters and associated levels are shown in Table 3.

TABLE 3

List of parameters and associated levels

| Variables | Low | Mid | High |
|---|---|---|---|
| pH | 7.5 | 10 | 12 |
| Concentration (M) | 0.01M | 0.5M | 1M |
| Contact time (min) | 10 min | 60 min | 110 min |

For all the runs standard flushing procedure described below was followed. All filters used were of same type and same lot (Viresolve Pre Filter OptiScale 40 Capsule Cat No SSPVA40NB9, Lot No C6BA18393)). 100 L/m² specialized solution flush was performed at 200 LMH flux with the given concentration and pH. Static hold was performed for the given time as per DOE. After static flush, 400 L/m² water flush was performed at 600 LMH. Filters were then conditioned with 50 mM acetate buffer 80 mM sodium chloride pH 5.5 buffer by flowing through 30 L/m² of buffer at 600 LMH. Post buffer flush 30 L/m² monoclonal antibody feed was loaded at 100 LMH as a model protein. This protein load was collected and analyzed for leached beta-glucan concentration. Charles River PTS Rapid Micro Method Glucan assay was used for beta-glucan analysis.

To compare the effectiveness of carbonate flush relative to water a negative control experiment was performed. For water control experiment 100 L/m² water was flushed through the filter at 200 LMH. Static hold for 60 minutes was performed. After static flush, 400 L/m² water flush was performed at 600 LMH. Filters were then conditioned with 50 mM acetate buffer 80 mM sodium chloride pH 5.5 buffer by flowing through 30 L/m² of buffer at 600 LMH. Post buffer flush 30 L/m² monoclonal antibody feed was loaded at 100 LMH as a model protein. This protein load was collected and analyzed for leached beta-glucan concentration. Charles River PTS Rapid Micro Method Glucan assay was used for beta-glucan analysis.

In addition to water control a standard flush experiment was also performed. This was done for comparing the specialized flush results with what is currently used in industry. For standard flush, flushing procedure included 100 L/m² of water flush followed by 30 L/m² of buffer flush both performed at 600 LMH. Post buffer flush 30 L/m² monoclonal antibody feed was loaded at 100 LMH as a model protein. This protein feed was collected and tested for leached beta-glucan content.

Glucan concentrations obtained from the study are shown in Table 4.

TABLE 4

Effect of concentration, static hold time and pH of sodium carbonate solution for beta-glucan removal.

| Run Number | Solution concentration (M) | Solution pH | Static hold time (min) | Beta-glucan Concentration | % reduction Beta-glucan Content compared to standard flush control | % reduction Beta-glucan Concentration compared to water control |
|---|---|---|---|---|---|---|
| 1 | 1 | 10 | 10 | 166.5 | 68 | 78 |
| 2 | 0.505 | 12 | 10 | 134 | 74 | 83 |
| 3 | 0.505 | 12 | 110 | 135.5 | 74 | 82 |
| 4 | 1 | 7.5 | 60 | 394.5 | 25 | 49 |
| 5 | 0.505 | 10 | 60 | 195 | 63 | 75 |
| 6 | 0.01 | 7.5 | 60 | 625.5 | −19 | 19 |
| 7 | 0.5 | 7.5 | 10 | 313.5 | 40 | 59 |
| 8 | 0.5 | 10 | 60 | 169.5 | 68 | 78 |
| 9 | 0.5 | 10 | 60 | 162 | 69 | 79 |
| 10 | 0.01 | 10 | 10 | 196.5 | 63 | 74 |
| 11 | 1 | 10 | 110 | 203.5 | 61 | 74 |
| 12 | 0.5 | 7.5 | 110 | 585 | −12 | 24 |
| 13 | 0.01 | 10 | 110 | 155.5 | 70 | 80 |
| 14 | 1 | 12 | 60 | 212 | 60 | 72 |
| 15 | 0.01 | 12 | 60 | 125 | 76 | 84 |
| 16 | Water Flush | | | 769 | | |
| 17 | Standard flush | | | 524 | | |

Figure 7:
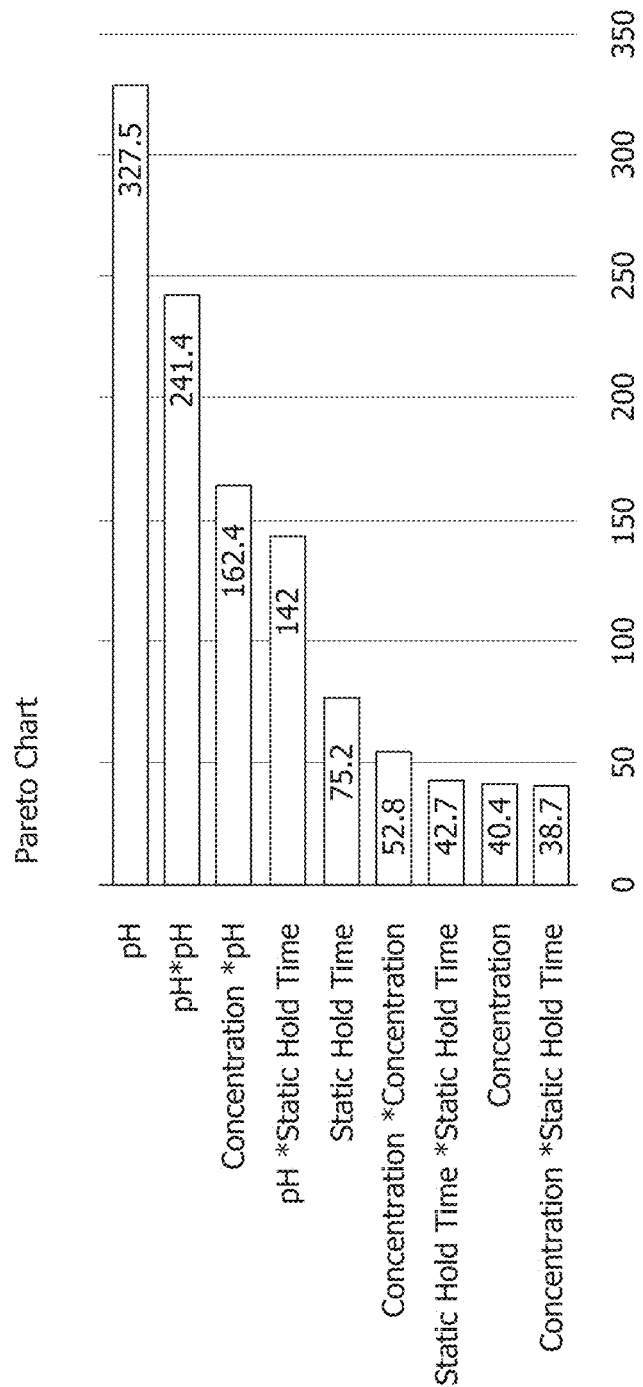
FIG. 7 is a graph illustrating a Pareto chart for size of effect analysis.

DOE was analyzed for identifying the significant parameters and their impact on the removal of beta-glucans from depth media. Analysis of variance was performed to identify the parameters which are statistically significant in the model. Solution pH was identified as the most significant process variable and solution concentration did not have significant impact by itself but pH and concentration interaction term was significant. Linear and squared terms for static hold time did not have a statistically significant effect on the leached beta-glucan but the interaction term pH*static hold time was significant. Size of effects for different terms are shown in Pareto Chart in FIG. 7. Terms represented by blue bars were statistically significant.

Regression equation representing the relationship between levels of beta-glucan which can potentially leach into protein and the factors analyzed in the DOE is given by Equation 1.

$$\text{beta-glucan} = 3154 - 908 \text{ Concentration} - 536.7 \text{ pH} + 7.54 \text{ Static Hold Time} + 107.8 \text{ Concentration}*\text{Concentration} + 23.84 \text{ pH}*\text{pH} - 0.00854 \text{ Static Hold Time}*\text{Static Hold Time} + 72.9 \text{ Concentration}*\text{pH} + 0.782 \text{ Concentration}*\text{Static Hold Time} - 0.631 \text{ pH}*\text{Static Hold Time} \quad (1)$$

Figure 8:
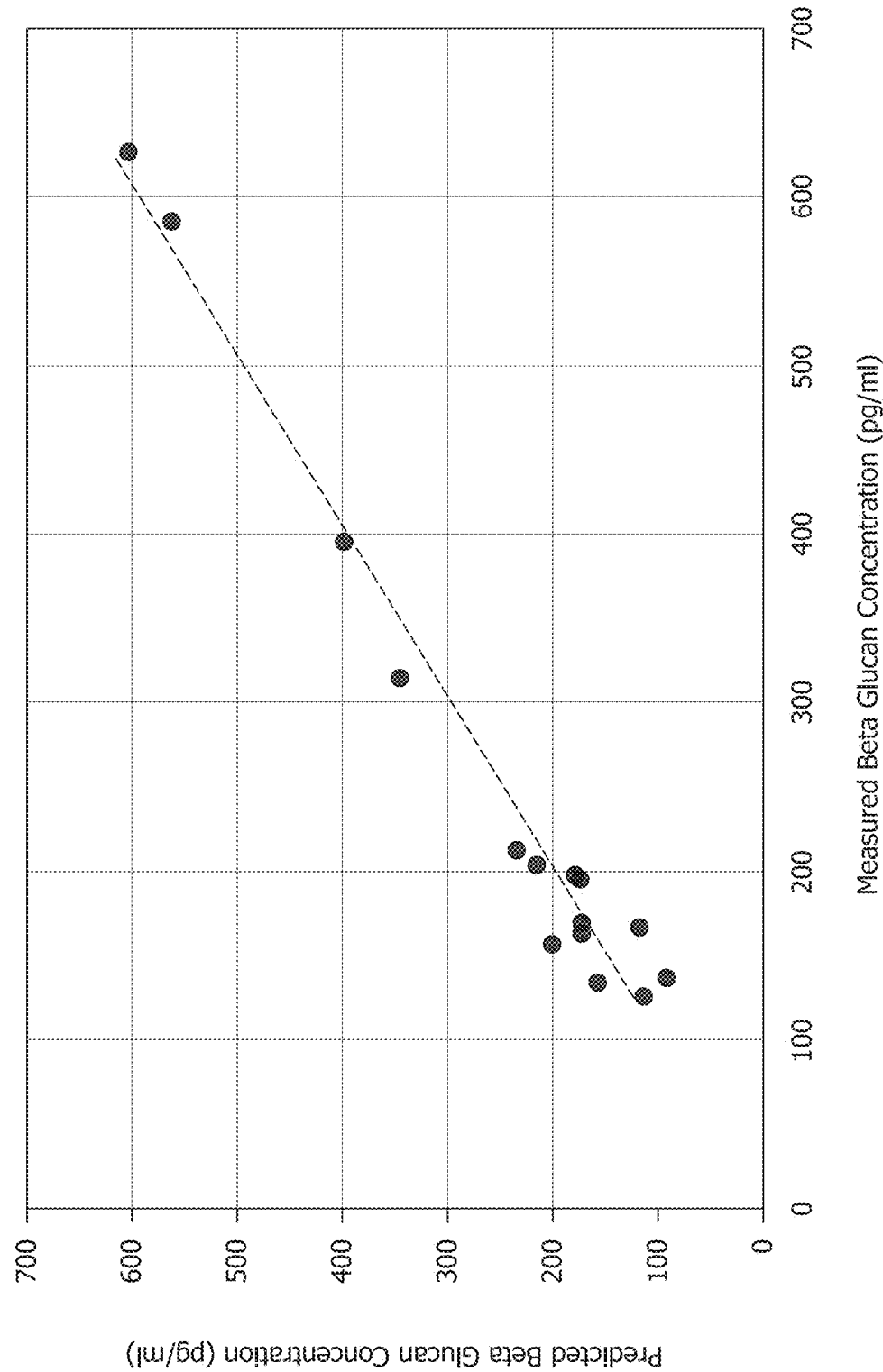
FIG. 8 is a graph illustrating measured versus predicted beta-glucan leachable level.

Plot of predicted versus measured leached beta-glucan concentration is shown in FIG. 8.

Contour plots were generated to visualize the effect of parameters with three hold conditions as shown in Table 5.

TABLE 5

Hold values for contour plots

| Hold Level | pH | Concentration (M) | Static hold time (min) |
|---|---|---|---|
| Low | 7.5 | 0.001 | 10 |
| Intermediate (Center) | 10 | 0.5 | 60 |
| High | 12 | 1 | 110 |

Figure 9:
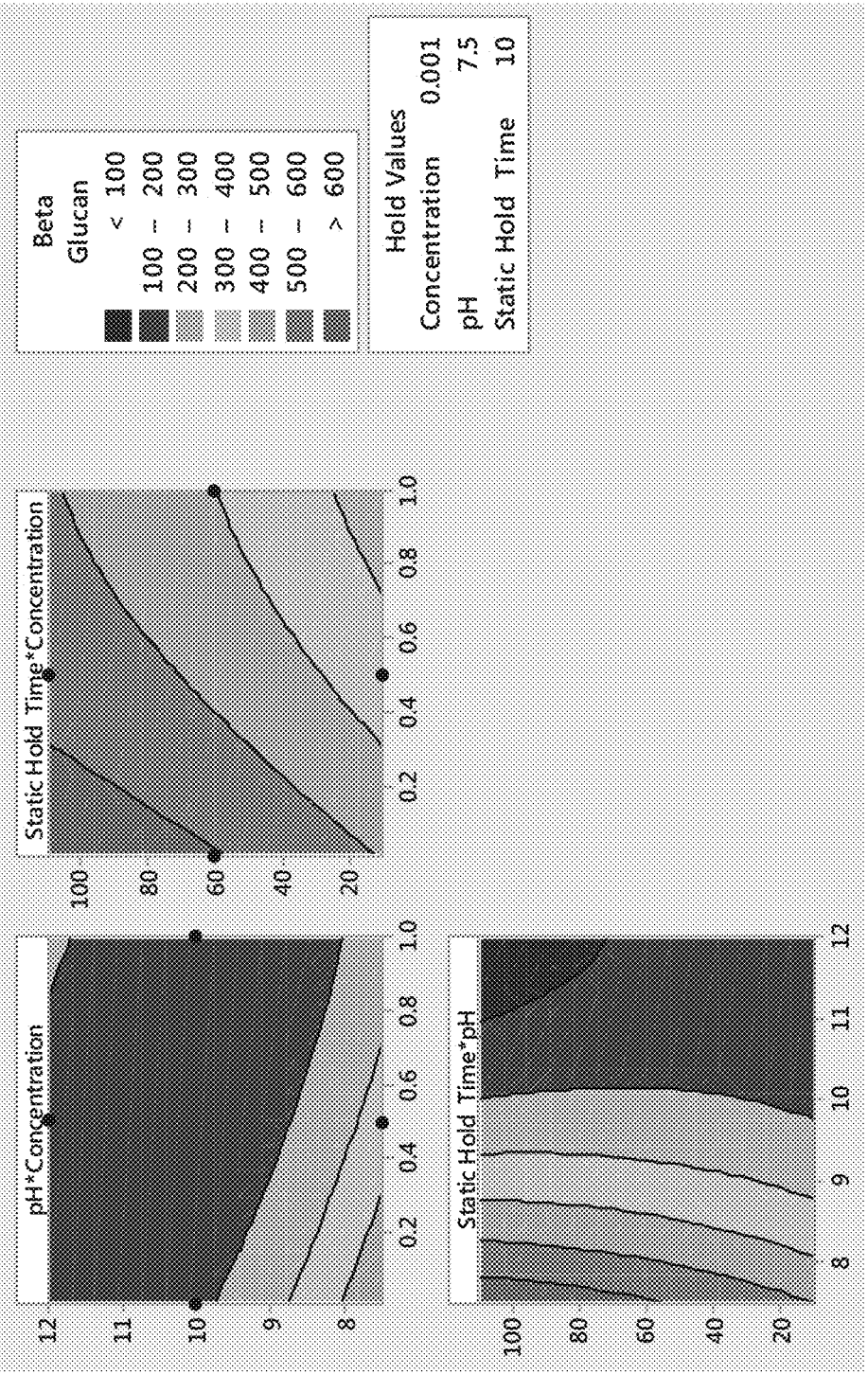
FIG. 9 is a contour plot illustrating low hold values.

Contour plot for low hold values is shown in FIG. 9. pH* concentration plot (top, left) shows at hold time of 10 minutes, leached beta-glucan concentration of can be reduced to 100-200 pg/ml range by solution pH greater than 10. Lower pH carbonate solution (<10) require higher concentration (>0.5 M) to reduce levels of leached beta-glucans. Static hold time* concentration plot (top, right) show low pH carbonate solution (pH 7.5) require concentration greater than 0.7 M to remove beta-glucans. Static hold time* pH plot (bottom, left) show that that at solution concentration of 10 mM, significant reduction in leached beta-glucans can be achieved at pH 9 or higher. Also under these conditions static hold time did not significantly impact the reduction in leached beta-glucan. Highest removal was achieved at pH 11 or higher with extended static hold times 80-110 minutes.

Figure 10:
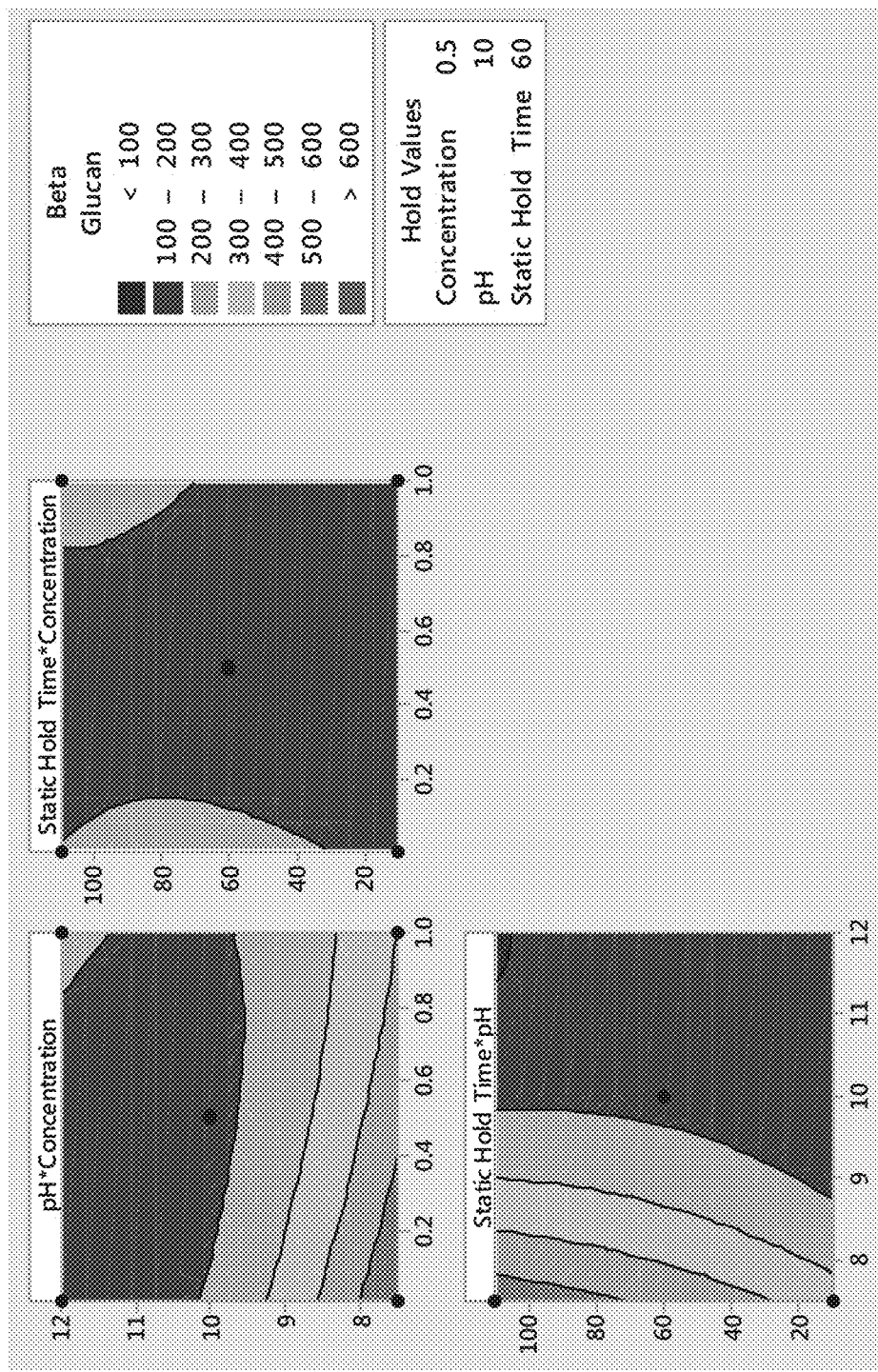
FIG. 10 is a contour plot illustrating intermediate hold values.

For Intermediate hold values the contour plots are shown in FIG. 10. pH* concentration plot (top, left) shows carbonate solution at pH 9.5 or greater is effective in reduction of leached beta-glucan across entire investigated solution concentration range (0.001 M to 1M) at 60 minute static hold time. pH 10 carbonate solution was effective in reduction of leached beta-glucan effectively over the entire hold time and concentration range as shown in static hold time *concentration plot (top, right). Static hold time * pH plot (bottom, left) shows that the pH 9.5 or higher is effective in reduction of leached beta-glucans at 0.5M concentration independent of static hold time.

Figure 11:
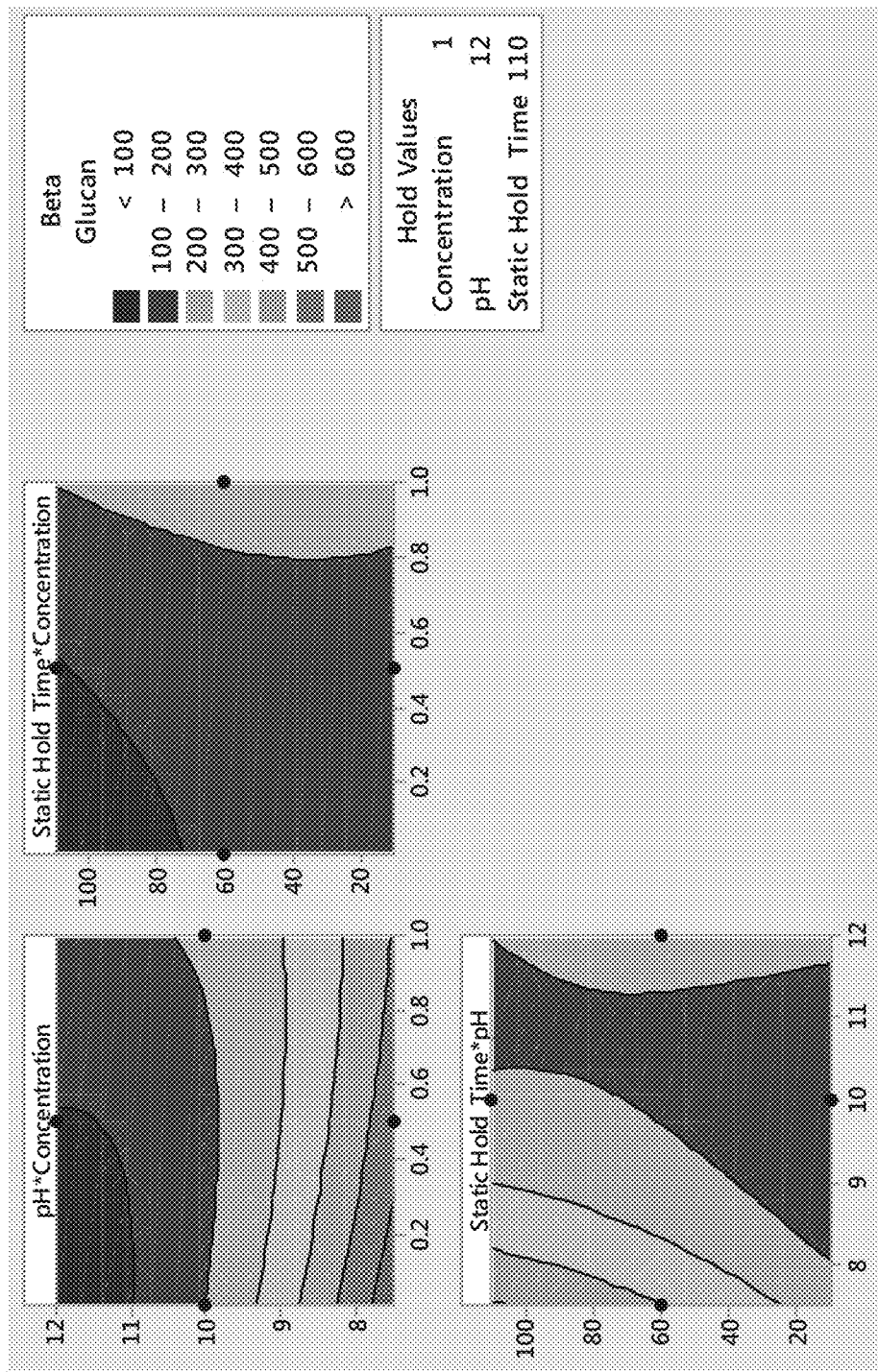
FIG. 11 is a contour plot illustrating high hold values.

For high hold values the contour plots are shown in FIG. 11. pH* concentration plot (top, left) shows carbonate solution at pH 9.5 or greater is effective in reduction of leached beta-glucans across entire investigated solution concentration range (0.001M to 1M) at 110 minute static hold time. Additionally pH 11-12 and concentration 0.001 M to 0.5 M range can reduce the leached beta-glucan concentration to below 100 pg/ml. pH 12 carbonate solution was effective in removing beta-glucans effectively over the entire hold time and concentration range as shown in static hold time *concentration plot (top, right). Concentration below 0.5M at pH 12 at static hold time greater than 75 minutes was most effective for removing beta-glucans. Static hold time * pH plot (bottom, left) shows that solution concentration of 1M, pH 8.5 or higher is effective in reducing leached beta-glucan levels to below 200 pg/ml.

3. Evaluation of Flushing in Recirculation Mode

In this study we investigated if flushing can be carried out in a recirculation mode as compared to flow through mode as in case of Example 1 and Section 1 and 2 of Example 2. Recirculation mode can help reduce the solution volume needed to perform the flush on depth filters installed in a GMP setting.

Figure 12:
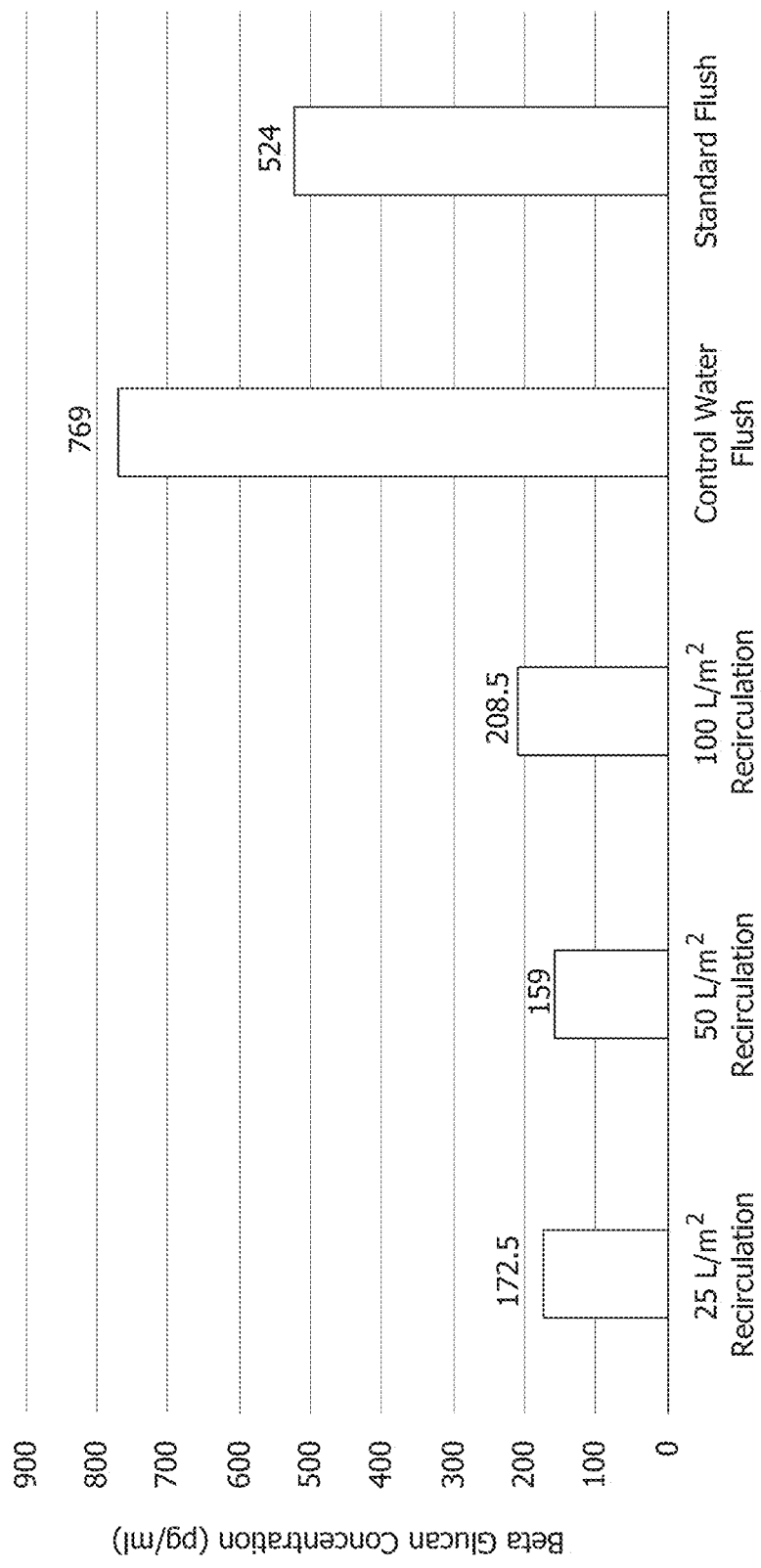
FIG. 12 is a graph illustrating the effect of different volume to area ratio of flushing solution in recirculation mode.

Three different volume to area ratios were tested in recirculation mode. 25 L/m$^2$, 50 L/m$^2$ and 100 L/m$^2$. Solution flush was performed at 200 LMH flux. No static hold was performed. After solution flush, 400 L/m$^2$ water flush was performed at 600 LMH. Filters were then conditioned with 50 mM acetate buffer 80 mM sodium chloride pH 5.5 buffer by flowing through 30 L/m$^2$ of buffer at 600 LMH. Post buffer flush 30 L/m$^2$ monoclonal antibody feed was loaded at 100 LMH as a model protein. This protein load was collected and analyzed for leached beta-glucan. Results are shown in FIG. 12. All three volume to area ratio were able to reduce the levels of leached beta-glucan to 100-200 pg/ml range. The water control and standard flush data shown in FIG. 12 is from Example 2 Section 2.

Example 3: Reduction Beta-Glucan from Cellulose Pulp Used for Filter Media

In this example, effectiveness of potassium carbonate and sodium carbonate for reduction of beta-glucan from cellulose pulp used to make filter media was investigated. Pulp was received in form of flat sheets. 47 mm discs were punched out using a 47 mm Arch Punch. Discs were installed in Millipore Corporation stainless steel filter holder CAT No XX4404700. One disc was installed in each holder. Four parallel filtration trains were set up using automated data acquisition system for collecting pressure and flowrate data similar to Example 1 and 2. 0.5 M sodium carbonate pH 10 and 0.5 M potassium carbonate pH 10, 0.5 N sodium hydroxide were tested during this study. Water was used as a negative control.

Figure 13:
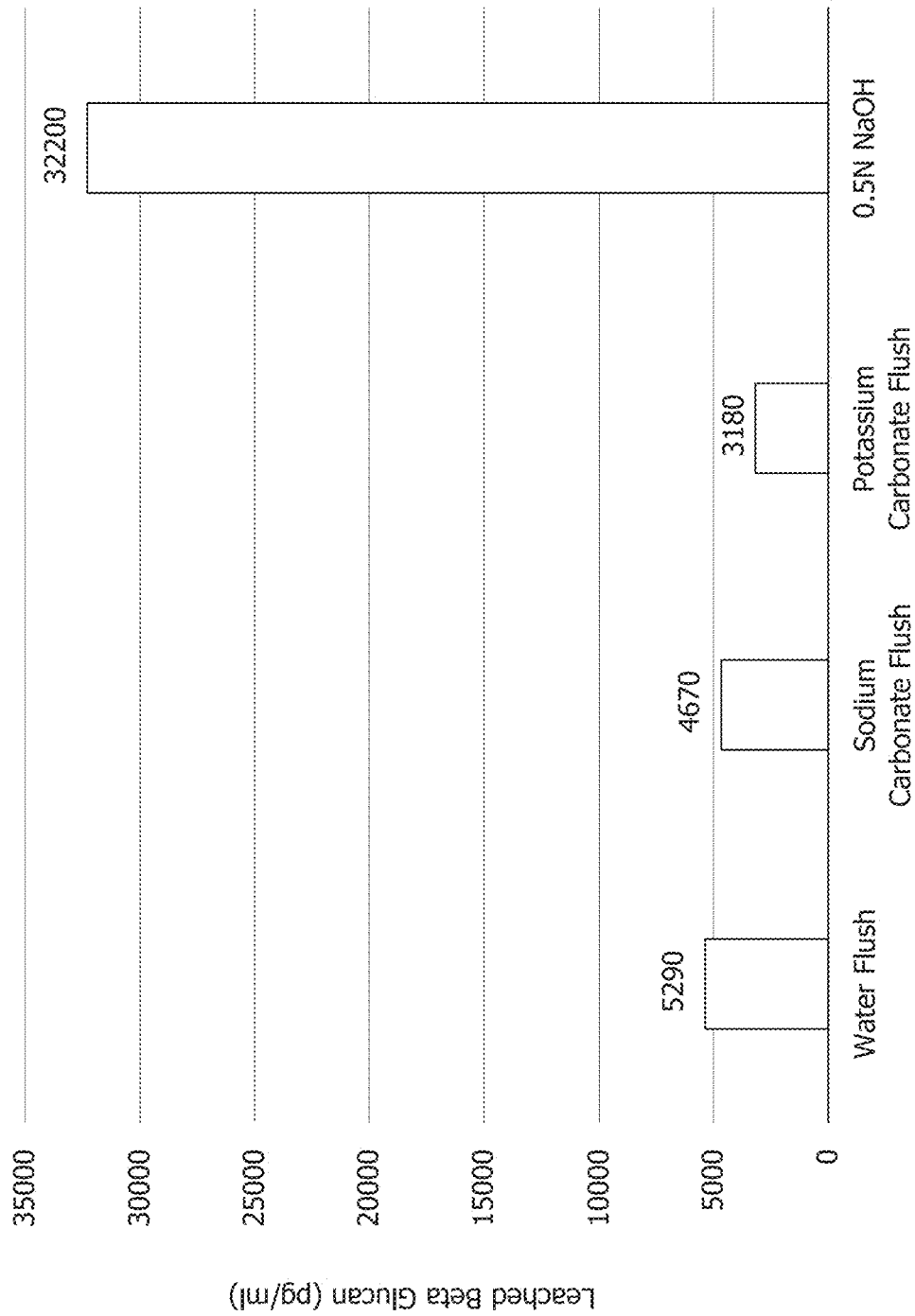
FIG. 13 is a graph illustrating the reduction of leached beta-glucan from unprocessed cellulose pulp using sodium and potassium hydroxide.

Flushing sequence included 100 L/m$^2$ solution flush (water in case of negative control) was performed at 200 LMH flux. 60 minute static hold was performed. After static hold, 400 L/m$^2$ water flush was performed at 600 LMH. Pulp was conditioned with 50 mM acetate buffer 80 mM sodium chloride pH 5.5 buffer by flowing through 30 L/m$^2$ of buffer at 600 LMH. Post buffer flush 30 L/m$^2$ monoclonal antibody feed was loaded at 100 LMH as a model protein. This protein load was collected and analyzed for leached beta-glucans. Charles River PTS Rapid Micro Method Glucan assay was used for beta-glucan analysis. The sodium and potassium carbonate flush were able to reduce leached beta-glucan levels by 620 pg/ml and 2110 pg/ml respectively. 0.5N NaOH resulted in increase the leached beta-glucan level. Results are shown in FIG. 13.

What is claimed is:

1. A method for reducing the amount of leachable beta-glucans in a cellulose-containing filter material, the method comprising treating the filter material with a solution comprising a carbonate salt, an organic carbonate, or carbonic acid.

2. The method of claim 1, wherein the solution comprises a carbonate salt selected from the group consisting of ammonium carbonate, ammonium hydrogen carbonate, barium carbonate, calcium carbonate, iron carbonate, lithium carbonate, magnesium carbonate, manganese carbonate, potassium carbonate, potassium hydrogen carbonate, sodium carbonate, sodium hydrogen carbonate, and mixtures thereof.

3. The method of claim 2, wherein the carbonate salt is selected from the group consisting of ammonium carbonate, calcium carbonate, iron carbonate, magnesium carbonate, manganese carbonate, potassium carbonate, sodium carbonate, and mixtures thereof.

4. The method of claim 3, wherein the carbonate salt is selected from the group consisting of ammonium carbonate, calcium carbonate, potassium carbonate, sodium carbonate, and mixtures thereof.

5. The method of claim 4, wherein the carbonate salt is sodium carbonate, potassium carbonate, or a mixture thereof.

6. The method of claim 1, wherein the solution comprises an organic carbonate which is a carbonate ester selected from the group consisting of dimethyl carbonate, diphenyl carbonate, ethylene carbonate, trimethylene carbonate, propylene carbonate, glycerol carbonate, and mixtures thereof.

7. The method of claim 1, wherein the pH of the solution is in the range from about 7.5 to about 12.

8. The method of claim 7, wherein the pH of the solution is in the range from about 8.5 to about 12.

9. The method of claim 8, wherein the pH of the solution is in the range from about 10 to about 12.

10. The method of claim 1, wherein the solution comprises a carbonate salt or an organic carbonate, and a carbonate concentration of the solution is from about 0.01 M to about 0.5 M.

11. The method of claim 1, wherein the solution comprises a carbonate salt or an organic carbonate, and a carbonate concentration of the solution is from about 0.01 M to about 1 M.

12. The method of claim 1, wherein the treatment comprises immersing the filter material in the solution for about 1 minute to about 240 minutes.

13. The method of claim 12, wherein the treatment comprises immersing the filter material in the solution for about 60 minutes to about 120 minutes.

14. The method of claim 1, wherein the filter material includes cellulose fibers selected from: wood pulp derived or cotton derived fibers; regenerated cellulose fibers; cellulose fibers combined with inorganic filter aids selected from the group consisting of diatomaceous earth, perlite, and fumed silica; cellulose fibers combined with inorganic filter aids and organic resins; fibers of cellulose/silica blends; fibers of cellulose derivatives selected from cellulose acetate or cellulose triacetate; or any combination thereof.

15. The method of claim 1, wherein the filter material is a depth filter material.

16. The method of claim 1, wherein the filter material is a depth filter, the filter material being included in a housing.

17. The method of claim 1, wherein the filter material is a wood pulp.

18. A method for preparing a biopharmaceutical or a plasma derivative having a reduced amount of leached beta-glucan compared to the biopharmaceutical or a plasma derivative after contact with cellulose-containing filter material not treated in accordance with claim 1, the method comprising treating the biopharmaceutical or a plasma derivative by contact with the cellulose-containing filter material treated in accordance with claim 1.

* * * * *